US011940650B2

United States Patent
Won

(10) Patent No.: US 11,940,650 B2
(45) Date of Patent: *Mar. 26, 2024

(54) MOBILE-PLATFORM COMPRESSION-INDUCED IMAGING FOR SUBSURFACE AND SURFACE OBJECT CHARACTERIZATION

(71) Applicant: Temple University—Of The Commonwealth System Of Higher Education, Philadelphia, PA (US)

(72) Inventor: Chang-Hee Won, Maple Glen, PA (US)

(73) Assignee: TEMPLE UNIVERSITY—Of The Commonwealth System of Higher Education, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/957,178

(22) Filed: Sep. 30, 2022

(65) Prior Publication Data

US 2023/0037458 A1  Feb. 9, 2023

Related U.S. Application Data

(63) Continuation of application No. 16/634,445, filed as application No. PCT/US2018/043910 on Jul. 26, 2018, now Pat. No. 11,457,815.

(Continued)

(51) Int. Cl.
*G02B 6/10* (2006.01)
*A61B 5/00* (2006.01)
(Continued)

(52) U.S. Cl.
CPC .............. *G02B 6/10* (2013.01); *A61B 5/0053* (2013.01); *A61B 5/0059* (2013.01); *A61B 5/444* (2013.01);
(Continued)

(58) Field of Classification Search
CPC ....... G02B 6/10; A61B 5/0053; A61B 5/0059; A61B 5/444; A61B 5/6843; A61B 5/6898;
(Continued)

(56) References Cited

U.S. PATENT DOCUMENTS 6,264,610 B1  7/2001  Zhu
8,699,661 B2  4/2014  Jang et al.
(Continued)

FOREIGN PATENT DOCUMENTS

JP  2012170744 A  9/2012
KR  10-2012-0010585 A  2/2012
(Continued)

OTHER PUBLICATIONS

Hosseini et al., "A medical tactile sensing instrument for detecting embedded objects, with specific application for breast examination", The International Journal of Medical Robotics and Computer Assisted Surgery (2010), vol. 6, pp. 73-82.
(Continued)

*Primary Examiner* — Hien N Nguyen
(74) *Attorney, Agent, or Firm* — Faegre Drinker Biddle & Reath LLP

(57) ABSTRACT

A mobile-platform imaging device uses compression of the target region to generate an image of an object. A tactile sensor has an optical waveguide with a flexible, transparent first layer. Light is directed into the waveguide. Light is scattered out of the first layer when the first layer is deformed. The first layer is deformed by the tactile sensor being pressed against the object. A force sensor detects a force pressing the tactile sensor against the object and outputs corresponding force information. A first communication unit receives the force information from the force sensor. A receptacle holds a mobile device with a second
(Continued)

communication unit and an imager that can generate image information using light scattered out of the first layer. The first communication unit communicates with the second communication unit and the mobile device communicates with an external network.

20 Claims, 14 Drawing Sheets

Related U.S. Application Data

(60) Provisional application No. 62/538,032, filed on Jul. 28, 2017.

(51) Int. Cl.
```
A61B 90/30      (2016.01)
G01N 3/08       (2006.01)
G01N 19/00      (2006.01)
G06T 7/00       (2017.01)
G06V 10/10      (2022.01)
G06V 10/147     (2022.01)
H04M 1/04       (2006.01)
```

(52) U.S. Cl.
CPC .......... *A61B 5/6843* (2013.01); *A61B 5/6898* (2013.01); *A61B 5/7267* (2013.01); *A61B 5/7275* (2013.01); *G01N 3/08* (2013.01); *G01N 19/00* (2013.01); *G06T 7/0012* (2013.01); *G06V 10/10* (2022.01); *G06V 10/147* (2022.01); *H04M 1/04* (2013.01); *A61B 5/0022* (2013.01); *A61B 2090/306* (2016.02); *A61B 2562/0238* (2013.01); *A61B 2576/00* (2013.01); *G06T 2207/30096* (2013.01); *H04M 2250/12* (2013.01)

(58) Field of Classification Search
CPC ... A61B 5/7267; A61B 5/7275; A61B 5/0022; A61B 2090/306; A61B 2562/0238; A61B 2576/00; A61B 2560/0233; A61B 2562/0233; A61B 5/0033; A61B 5/0062; A61B 5/0077; A61B 5/1079; A61B 5/4312; A61B 5/0013; G01N 3/08; G01N 19/00; G01N 3/24; G06T 7/0012; G06T 2207/30096; G06V 10/10; G06V 10/147; H04M 1/04; H04M 2250/12; G01S 7/00; G16H 30/20; G16H 40/40; G16H 50/30

See application file for complete search history.

(56) References Cited

U.S. PATENT DOCUMENTS

```
9,652,696   B2   5/2017   Won
10,311,343  B2   6/2019   Won
10,321,826  B2   6/2019   Won
2005/0277852 A1  12/2005  Shih et al.
2013/0070074 A1  3/2013   Won
2013/0199300 A1  8/2013   Abe
2013/0211285 A1  8/2013   Fuller et al.
2014/0009262 A1  1/2014   Robertson et al.
2015/0099973 A1  4/2015   Abe
2015/0320385 A1  11/2015  Wright
2015/0370320 A1  12/2015  Connor
2016/0228008 A1  8/2016   Lee
2017/0143208 A1  5/2017   Blank et al.
2017/0173262 A1  6/2017   Veltz
2019/0125245 A1  5/2019   Kim et al.
```

FOREIGN PATENT DOCUMENTS

```
KR   10-2012-0025653 A    3/2012
KR      10-1490126  B1    2/2015
KR      10-1504102  B1    3/2015
KR      10-1546403  B1    8/2015
KR      10-1626358  B1    6/2016
KR      10-1628990  B1    6/2016
KR      10-1964260  B1    4/2019
KR   10-2019-0048192 A    5/2019
KR      10-2018171  B1    9/2019
WO       2017003251 A1    1/2017
WO       2017090802 A1    1/2017
WO       2017090803 A1    1/2017
WO       2017025775 A1    2/2017
WO       2019078545 A1    4/2019
```

OTHER PUBLICATIONS

Lee et al., "Tactile Sensation Imaging System for Embedded Lesion Characterization", Transactions on Information Technology in BioMedicine, Manuscript ID TITB-00165-2012 (submitted May 6, 2012), 9 pgs.

Lee et al., "Tactile sensation imaging system for inclusion characterization", Proc. SPIE 7890, Advanced Biomedical and Clinical Diagnostic Systems IX 78901D (Feb. 21, 2011): doi: 10.1117/12.875347; http//dx.doi.org/10.1117/12.875347, 16 pgs.

J.-H. Lee and C.-H. Won, "High Resolution Tactile Imaging Sensor Using Total Internal Reflection and Non-rigid Pattern Matching Algorithm", IEEE Sensors Journal, vol. 11, No. 9, pp. 2084-2093 (published on-line Jan. 28, 2011), 10 pgs.

Lee et al., "Design and Evaluation of an Optical Tactile Imaging Device for Tumor Detection", 52nd Annual Meeting of American Association of Physicists and Medicine (AAPM), Philadelphia, PA (Jul. 18-22, 2010), 3 pgs.

Lee et al., "Tactile Sensation Imaging for Artificial Palpation", Eurohaptics 2010, Amsterdam, NL (Jul. 8-10), 6 pgs.

Lee et al., "Tactile Imaging Sensor for Subsurface Tumor Detection in Prostate Phantom", The First AMA-IEEE Medical Technology Conference on Individualized Healthcare, Washington, DC (Mar. 21-23, 2010), 1 pg.

Ohka et al., An Experimental Optical Three-axis Tactile Sensor Featured with Hemispherical Surface, Journal of Advanced Mechanical Design, Systems, and Manufacturing (2008), vol. 2, No. 5, pp. 860-873.

Oleksyuk et al., "Risk Score Based Pre-screening of Breast Tumor Using Compression Induced Sensing System", IEEE Sensors Journal (May 15, 2018) vol. 18, No. 10, pp. 4038-4045.

Oleksyuk et al., "Smartphone-based Compression-Induced Scope Prototype for Tumor Characterization", 38th Annual International Conference of the IEEE Engineering in Medicine and Biology Society, Orlando, FL (Aug. 16-20, 2016), 2 pgs.

Saga et al., "High-resolution tactile sensor using the deformation of a reflection image", Sensor Review 27.1 (2007): 35-42.

Sahu et al., "Characterization of Mammary Tumors Using Noninvasive Tactile and Hyperspectral Sensors", IEEE Sensors Journal (2014), vol. 14, No. 10, pp. 3337-3344.

Sahu et al., "Tactile and Hyperspectral Imaging Sensors for Mammary Tumor Characterization", Proceedings of IEEE Sensors Conference, Baltimore, MD. (Nov. 4-6, 2013), 4 pgs.

F. Saleheen and C. Won, "Bimodal Dynamic Imaging System for Embedded Inclusion Characterization", IEEE Sensors Journal (May 2016), vol. 16, No. 15, pp. 6062-6071.

F. Saleheen and C. Won, "Dynamic Imaging System for Mechanical and Spectral Properties Estimation", 2015 IEEE Biomedical Circuits and Systems Conference (BioCAS), Atlanta, GA (Oct. 22-24, 2015), 4 pgs.

F. Saleheen and C. Won, "Dynamic positioning sensing system for estimating size and depth of embedded object," 2015 IEEE Sensors Conference, Busan, Korea (Nov. 1-4), pp. 1-4.

Saleheen et al., "Noninvasive mechanical properties estimation of embedded objects using tactile imaging sensor", Proceedings of SPIE, vol. 8719, ISBN 9780819495105, SPIE Defense, Security,

(56) References Cited

OTHER PUBLICATIONS and Sensing Conference, Smart Biomedical and Physiological Sensor Technology X Conference, Baltimore, MD (May 2, 2013), p. 159.

Shen et al., "Quantification and Verification of Automobile Interior Textures by a High Performance Tactile-Haptic Interface", Proceedings of the 2006 IEEE/RSJ International Conference on Intelligent Robots and Systems, Beijing, China (Oct. 9-15, 2006), pp. 3773-3778.

Smith et al., "Cell-Phone-Based Platform for Biomedical Device Development and Education Application", PLoS One (2011), vol. 6, Issue 3, e17150, 11 pgs.

Won et al., "Tumor size and elasticity estimation using Smartphone-based Compression-Induced scope," 2017 39th Annual International Conference of the IEEE Engineering in Medicine and Biology Society (EMBC), (Jul. 11-15, 2017) pp. 4106-4109.

Zhang et al., "A Multi-Purpose Tactile Sensor Inspired by Human Finger for Texture and Tissue Stiffness Detection", Proceedings of the 2006 IEEE International Conference on Robotics and Biomimetics, Kinming, China (Dec. 17-20, 2006), pp. 159-164.

Canadian Office Action for related Canadian Application No. 3107765 dated Apr. 22, 2021, 8 pages.

Extended European Search report for related EP Application No. 18837690.9 dated May 25, 2022, 17 pages.

First Examination Report in India for related Indian Application No. 202017007945 dated Jul. 27, 2022 with Translation, 7 pages.

Indonesia Office Action for related Indonesia Application No. P00202001580 dated Oct. 6, 2022 with Translation, 4 pages.

Japanese Office Action for related JP Application No. 2020-504098 dated Jun. 21, 2022 with Translation, 15 pages.

Examination Report for corresponding EP Application No. 18837690.9 dated Nov. 17, 2023, 6 pages.

MOBILE-PLATFORM COMPRESSION-INDUCED IMAGING FOR SUBSURFACE AND SURFACE OBJECT CHARACTERIZATION

CROSS-REFERENCE TO RELATED APPLICATION

The present application is a continuation of U.S. application Ser. No. 16/634,445, filed Jan. 27, 2020, which is the national stage application of International Patent Application No. PCT/US2018/043910, filed Jul. 26, 2018, and claims priority to U.S. Provisional Application No. 62/538,032, filed Jul. 28, 2017. The disclosures of those patent applications are incorporated herein by reference in their entirety. The present application is related to and further develops the teaching of commonly invented and assigned International Patent Application No. PCT/US2011/043203, filed Jul. 7, 2011, and corresponding U.S. Pat. No. 9,652,696, issued May 16, 2017. The entire content of that application and patent are incorporated herein by reference in their entireties as if set forth explicitly herein.

STATEMENT OF GOVERNMENTAL INTEREST

The invention described herein was supported by United States Congressionally Directed Medical Research Programs Grant No. W81XWH-16-1-0035. The United States government has certain rights in the invention.

FIELD

The invention relates to compression-induced imaging and characterization of subsurface and surface objects, and especially to a mobile-platform based device and related method for determining the size and stiffness of a solid target below the surface of a softer solid medium. The device and method have applications in non-invasively characterizing tumors within the human or animal body.

BACKGROUND

Elasticity is one of the properties that are used in identifying malignant tumors. Unhealthy tissues tend to be stiffer than corresponding healthy tissues (Itoh et al. 2006, Dargahi 2004, Rivaz 2008, Krouskop 1998, Regini 2010). So, quantifying tissue elasticity would greatly aid medical practitioners in classifying and identifying unhealthy tissues.

One researcher has reported detecting 116 cases of malignancy out of 120 cases using the elasticity score from a sonoelastography (Regini 2010). Even though sonoelastography shows good results, there are limitations. The main limitation of elastography is that tissue compression influences elasticity score, which may lead to misdiagnosis (Itoh et al. 2006). Moreover, elastography requires a hospital setting with trained operators, which means that it is not portable, and is expensive and complicated to operate.

The Tactile Imaging System (TIS) of the above-mentioned earlier application No. WO 2012/006431 has a camera, a probe, and a force sensor, and it can be connected to a laptop computer. However, practical embodiments of that system were somewhat bulky, relatively expensive and complex. There is therefore still room for improvement.

SUMMARY

According to one aspect of the present application there is provided a mobile-platform imaging device that uses compression of the target region to generate an image of an object, comprising: a tactile sensor comprising an optical waveguide comprising at least a first layer that is flexible and transparent, and at least one light source configured to direct light into the optical waveguide. The waveguide is configured so that at least some of the light directed into the optical waveguide is scattered out of the first layer when the first layer is deformed, and wherein the first layer is deformed by the tactile sensor being pressed against the object; a rigid frame preferably that holds the waveguide, or the waveguide could be formed with sufficient rigidity to support the waveguide in use. A force sensor that detects a force being applied to press the tactile sensor against the object and outputs corresponding force information. A first communication unit is connected to receive the force information from the force sensor. A receptacle is provided for holding a mobile device with a second communication unit and an imager so positioned that the imager can generate image information using at least some of the light scattered out of the first layer; wherein the first communication unit is capable of communicating with the second communication unit and the mobile device is capable of communicating with an external network.

The mobile-platform imaging device may be combined with a mobile telephone as the mobile device. The mobile telephone may then be programmed to generate the image information (i.e., includes the imager) using at least some of the light scattered out of the first layer, to receive the force information, to synchronize the image information with the force information, and to transmit the associated information to an external device. The transmitted information may then further include information selected such as a current date, a current time, a user ID of a current user of the mobile device, and a target ID of the object.

The image information may be selected from the group consisting of a single image, multiple images, and a video image.

The mobile-platform imaging device may be programmed to exchange a plurality of messages with the external device, generate a hash from content of the plurality of messages, and encrypt the image and/or force information using an encryption key determined from the hash.

The force sensor may be between the tactile sensor and the receptacle for holding the mobile device. The mobile-platform imaging device may further comprise a housing, and the force sensor may then be between the housing and the receptacle for holding the mobile device.

According to another aspect, there is provided a method of determining the surface or subsurface size of the object using the above-mentioned mobile-platform imaging device, comprising: obtaining the image information and corresponding force information at a plurality of applied forces; and estimating the size of the target using 3D interpolation.

The obtaining step may comprise obtaining a series of images over a time period while varying the force and selecting images from a part of the time period over which the force varies with time more smoothly and/or more linearly than during other parts of the time period.

According to a further aspect, there is provided a method for aligning the light source of the above-mentioned mobile-platform imaging device, comprising applying the tactile sensor with a preselected force to a known object, processing the image information to identify an asymmetry of the scattered light, and adjusting the light source, or at least one of the light sources, to reduce the asymmetry.

One or more light source illuminating the optical wave guide; the wavelength of light can vary for different applications or multiple wavelengths of light can be used in a single embodiment and controlled to provide varying image responses. The optical waveguide is transparent and flexible with the optical waveguide and camera configured to have a line of sight to capture deflected light. The light source can have a diffuser to generate uniform light and/or filters could be added to control the light emission into or out of the waveguide. A diffuser can be a hollow tube where a light source is placed inside the tube or a white plastic/paper diffuser material placed between the light source and the waveguide.

The waveguide may be held in place by a rigid frame, where a clear transparent layer could be a part of the frame, such that when the waveguide is pressed against the area of interest, the front part or portion of the waveguide facing against that area of interest will deform, while the waveguide will have sufficient rigidity to maintain the line of sight between the waveguide and the camera to permit detection of deflected light and calculation of the applied force. The rigidity could be provided by the waveguide itself (i.e., the waveguide shaped/configured to provide stiffness), a glass or plastic plate behind the waveguide, or the camera lens itself. In one embodiment, there is shown a rectangular waveguide with a clear rigid backing. If the waveguide is bent to provide sufficient rigidity as shown in FIG. 3A, then a rigid clear backing layer will not be necessary.

According to another aspect, there is provided a method for detecting a cut or damage to the waveguide of the mobile-platform imaging device, comprising applying the tactile sensor with a preselected force to a known object, processing the image information to identify an asymmetry of the scattered light, and when the asymmetry exceeds a threshold, indicating a cut or damage to the waveguide.

According to a further aspect, there is provided a method of determining the softness of the target of the mobile-platform imaging device, comprising: determining a contact area from the image information, determining stress from a contact area of the tactile sensor and the force information, determining strain of the flexible waveguide from the image information and determined stress; and determining strain of the inclusion from the strain of the flexible waveguide, the contact area, and the stress.

The step of determining strain of the flexible waveguide may use at least one of a sum of intensities of pixels of the scattered light and an intensity of a maximum intensity pixel of the scattered light.

According to another aspect, there is provided a method of determining the absolute elasticity of the target using Compression-induced Imaging System (CIS) information, comprising a forward modeling approach using finite element method, followed by an inverse modeling approach with deep brief network.

According to a further aspect, a method of obtaining a tumor risk index for an object comprises at least one of: computing the tumor risk index as a weighted sum of a size and a stiffness of the object; and a machine learning method to determine the risk index using convolution neural networks.

According to another aspect, there is provided a method of communication, comprising, by a first device, exchanging a plurality of messages with a second device, generating a hash from content of the plurality of messages, and at least one of: encrypting information using an encryption key determined from the hash and sending the encrypted information to the second device; and receiving information from the second device and attempting to decrypt the information using an encryption key determined from the hash.

The smartphone platform removes the need for a laptop and a dedicated camera and makes possible a more compact and portable device. The smartphone attachment can be made with just the elastomer probe, the light source, and a frame. By leveraging the ubiquitous availability of smartphones in today's society, the Compression-Induced Imaging System (CIS) on a mobile platform may be orders of magnitude more cost-effective than a stand-alone Tactile Imaging System. The smartphone already has a processor, a camera, and a transceiver capable of both short-range (Bluetooth, Wi-Fi) and long-range (cellular) communication. By making use of those, the cost, weight, and bulk of providing dedicated devices in the CIS unit are saved.

The optical waveguide could be automatically moved with a click of a switch towards the target by a motor (such as a linear actuator or screw drive, or through the use of pulleys or timing belts). This will allow automatic force application instead of pressing manually. In one application, the motor drives the optical waveguide toward the target area in a uniform motion of about 5 to 7 mm in approximately three seconds to obtain the tactile images.

The optical waveguide could have different shapes, such as semi-spherical, semi-cylindrical, or rectangular. It is also possible for a waveguide to be bent to provide sufficient rigidity, for example, the waveguide could be a substantially planar sheet that is then bent into a semi-cylindrical shape, with the shape imparting stiffness (i.e., structural rigidity) to the waveguide. The waveguide's front surface will touch the target area and the back surface will provide sufficient rigidity to obtain tactile images.

The images, pressure readings, and meta-data may be sent to the cloud. The utilization of the cloud as an intermediary "second device" is a highly beneficial step. That allows us to use the Compression-Induced Imaging System in any location, at any time, without needing to ensure that a physical recipient computer is available and on-line. The data can then be retrieved from the cloud for processing at the recipient computer at a later time.

In an embodiment, the device includes the elastomer light guide and the light source in front of a smartphone and a handle and a force sensor on the back, with the smartphone sliding into a slot between. The force is applied from the back, and the applied force, measured by the force sensor, is wirelessly transmitted to the smartphone application. A microcontroller with Bluetooth capabilities is used to transmit the applied force information to the smartphone, avoiding the need for a mechanical data connection, and thus the problem of ensuring that the correct connector is available for a specific smartphone. The elastomer is positioned so that the smartphone camera is aligned on the center of the elastomer. Force and image synchronization issues are solved using a smartphone application ("app") that both initiates the taking of the tactile image and polls for the applied force information. Then the applied force information is sent to the app via Bluetooth communication. Stored images and metadata (user number, case number, tumor location, date, time, applied force) are encrypted by the app and wirelessly transmitted to a Cloud server. Then, a local processing computer will download the data and process the data. The malignancy score will be computed, and the encrypted score will be sent back to the smartphone.

Under ideal conditions, a malignancy score can be computed and returned to the smartphone in near real time. However, if any of the communication links between the smartphone and the local processing computer is unavailable, then the data can be held, and forwarded when the required communication link comes up.

The "tumor risk index" aggregates all the determined mechanical properties into one number. This number will be used to judge the probability that the lump being examined is a malignant tumor.

The Mobile-platform Compression-induced Imaging System can emulate a human finger in detecting the mechanical properties (size, shape, stress, strain, mobility, and elasticity) of an object. The object can be directly touching the probe or indirectly compressed by the system.

This application relates to a system that characterizes certain mechanical properties of objects through applying gentle pressure from an overlying surface. A device that estimates surface or subsurface target size and softness will be useful in various applications. By basing that device on a mobile platform, such as a smartphone, the technology is made more readily accessible. The Compression-induced Imaging System (CIS) allows an operator to quickly capture the mechanical properties of a compressed object, with the convenience of a mobile platform.

The present system is inspired by some of the previously proposed systems, but with important differences. The present system uses a dynamical optical sensing mechanism and not a static electromechanical pressure sensor. This allows us to dynamically image and estimate mechanical properties more accurately. Furthermore, our system utilizes sensors and communication equipment of a mobile device to reduce the cost and increase accessibility.

One possible application of the Mobile-platform Compression-induced Imaging System (CIS) is detection of malignant human tumors. An embodiment of the new mobile system is therefore geared towards medicine for its potential to aid physicians in prescreening of tumors and for training in the technique of palpation. The mechanical properties this system could provide are a valuable resource in the tumor screening process.

DETAILED DESCRIPTION

Figure 1:
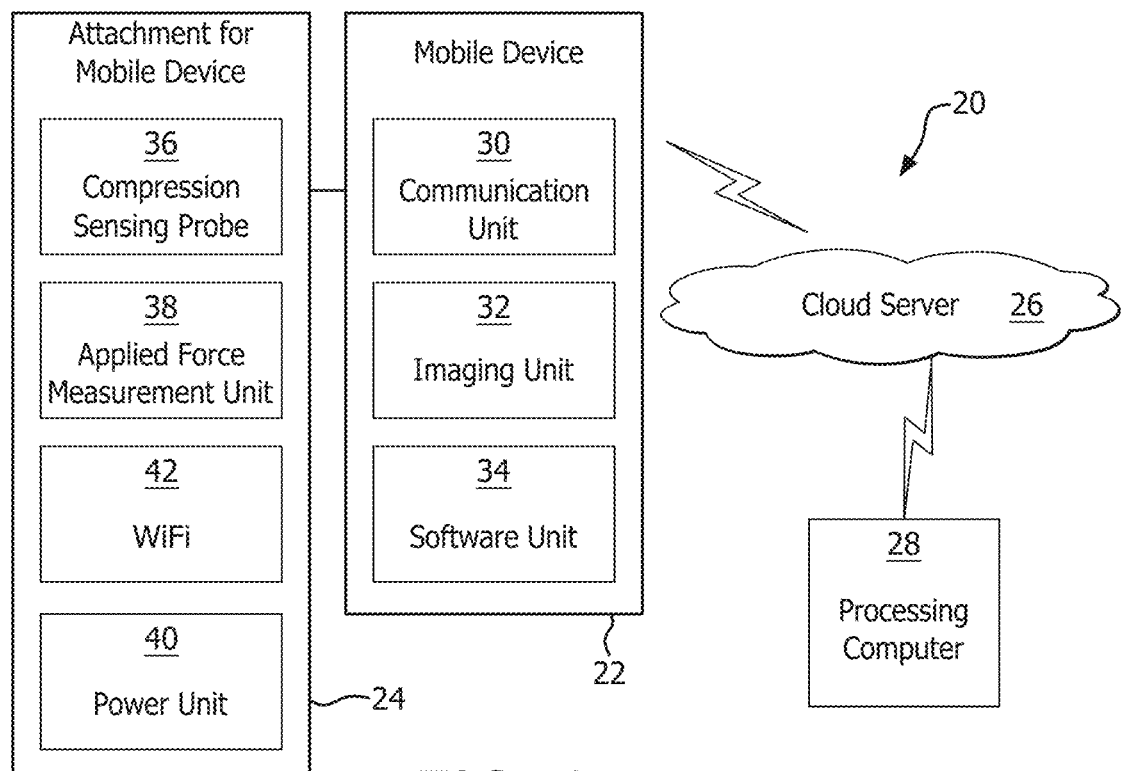
FIG. 1 shows an overall architecture of an embodiment of a mobile-platform compression-induced imaging system (CIS).

Referring to the drawings, and initially to FIG. 1, one embodiment of an overall architecture of a mobile-platform Compression-induced Imaging System (CIS), indicated generally by the reference numeral 20, consists essentially of a mobile device 22, a frontend attachment 24 to the mobile device 22, a cloud server 26, and a local processing unit 28. The mobile device 22 comprises an imaging unit, typically a camera, 32, a software unit 34, and a wireless communication unit 30, all of which are standard in smartphones, and in the interests of conciseness are not further described.

Figure 2:
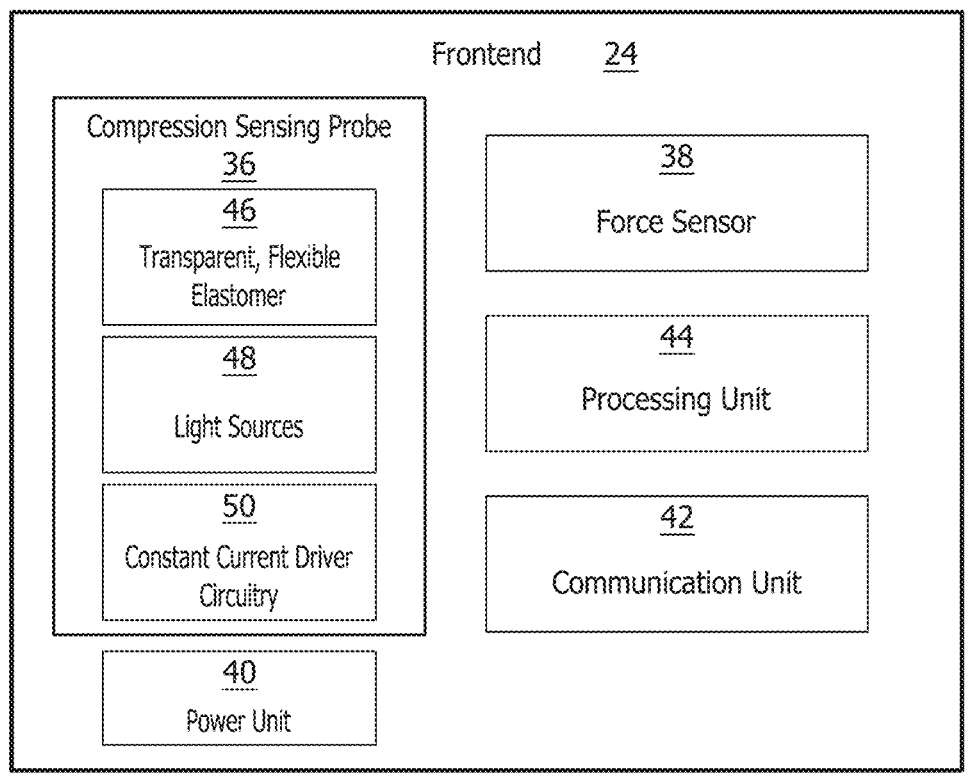
FIG. 2 is a block diagram of an embodiment of a front end attachment of the system shown in FIG. 1.

The frontend attachment 24 comprises a compression sensing probe 36, an applied force measurement unit 38, a power unit 40, a wireless communication unit 42, and a processing unit 44 (see FIG. 2).

The frontend attachment 24 is where all physical data acquisition (force and image data) takes place and provides a chassis for the mobile device (iPhone or other smartphone) 22. The processing unit (microcontroller) 44 communicates with the software unit 34 of the smartphone 22 via Bluetooth. The smartphone 22 communicates all data and metadata to the cloud server 26 via Wi-Fi if available, otherwise by cellular data transfer.

As will be described in more detail below, the frontend attachment 24 at least partially encases or mounts to the smartphone 22, in order to ensure accurate alignment between the compression sensing probe 36 and the camera 32, which must image the probe 36. The microcontroller 44 makes the force sensor readings possible and allows for Bluetooth communication with the smartphone software unit (app) 34. The data collection and image capture are controlled by the user within the app 34, using the user interface of the smartphone (see FIG. 12). When the user has collected desired data, the user can then send it (or it could automatically be sent at periodic intervals) via Wi-Fi to the cloud server 26.

The cloud server 26 comprises a cloud-based database, which may be conventional, and is not shown in detail. The database is used for storage of the tactile images and metadata until the local computer 28 is ready to process the data. The processed data is then returned to the originating smartphone 22. The user of the system is able to obtain the desired information on the screen of smartphone 22.

Referring now also to FIG. 2, the front end attachment 24 includes the compression sensing probe 36, which comprises a layer of transparent, flexible elastomer 46 and one or more light sources 48 for feeding light into the elastomer 46. In an embodiment the light sources 48 are light emitting diodes, which require constant-current driver circuitry 50. Other light sources may of course require different driver and control circuitry. The compression sensing probe 36 is shown in more detail in FIG. 7.

The transparent, flexible elastomer layer 46 forms an elastic optical waveguide, which is a primary functional component of a main sensing probe 36 of the device 20. In one embodiment of this probe 36, the optical waveguide 46 is an elastomer such as Polydimethylsiloxane (PDMS), which consists mainly of [—Si(CH$_3$)$_2$—], with a backing layer 72 (see FIG. 7) of glass or plastic, though again such is not necessary in all embodiments. The probe 36 generates light corresponding to the compression of the elastomer layer 46. The compression sensing is based on the optical phenomenon known as total internal reflection. If two different mediums have different indices of refraction, and a ray of light is shone through those two mediums then, when the ray reaches the interface between the two mediums, usually a fraction of light is transmitted with refraction and the rest is reflected, the amounts depending on the angle of incidence. However, if the ray starts in the medium of higher refractive index, there is a critical angle above which the refraction becomes impossible, and the ray is completely reflected, i.e., total internal reflection. In the present device, the elastomer layer 46 is configured so that the light from the light sources 48 is channeled along the layer between the PDMS-air interface at the front and the glass/plastic-air interface at the back by total internal reflection, provided that the elastomer layer 46 is not distorted. Elastomer waveguides are described in U.S. Pat. No. 9,652,696.

However, when the elastomer layer 46 of the probe 36 is compressed or deformed due to applied force, light is internally reflected off the distorted front surface at a steeper angle, at which some of the light escapes through the back glass/plastic-air interface of the elastomer layer. Some of this escaping light is captured by the imager 32 in the mobile device 22.

Figure 3C:
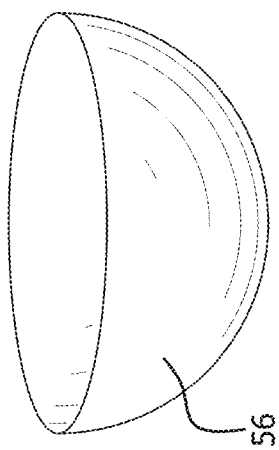
FIGS. 3A to 3C show elastomeric sensor elements for the front end attachment of FIG. 2.
Figure 3B:
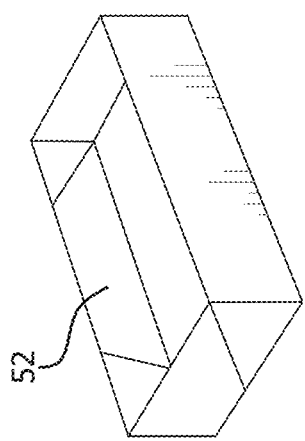
Figure 3A:
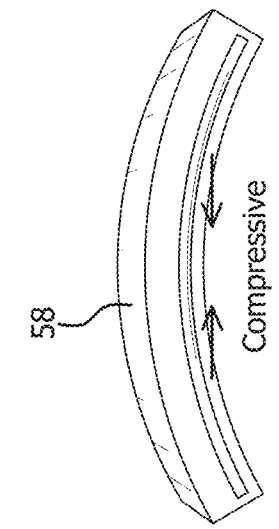

Referring also to FIGS. 3A to 3C, collectively FIG. 3, possible embodiments of the elastomer layer 46 include a rectangular shaped elastomer 52, a half sphere 56, and a rectangular shape curved into part of a cylinder 58. The sheets 52 and 58 have light sources 48 positioned so that the light enters from the boundaries at the narrow edges, nearly enough parallel to the large faces that the light is guided by total internal reflection. In the curved shape 56 (and 58 if the light is directed in the circumferential direction), the light is injected near the convex face, nearly enough tangential to the surface that it can be guided round the curve by total internal reflection. In all of these embodiments, there is a glass or plastic plate in between the elastomer and the camera. The plate can be flat, or can be curved, for example, to match the curvature of elastomer sheet 58. For all the elastomers the light is injected from the side to introduce as much internal reflection as possible.

The elastomer component 46 is held in place, and in shape, by a frame (see FIG. 7) that also provides a mounting for the light sources 48. This frame may have a clear, rigid layer 72 (e.g. glass or plastic) in between the optical waveguide 46 and the camera 32. Another embodiment is a curved elastomer 58 such as shown in FIG. 3A held by a rigid frame. The requirement is that there is a line of sight between the optical waveguide and the camera for capturing deflected light waves.

Various different light sources 48 can be used. The described embodiment uses ultra-bright white LEDs. The major function of the LEDs is to provide a full integration of light to illuminate the entire area of the sensing probe 36. The intensity of each individual LED affects the pixel value of each captured image. Therefore, having a uniform intensity in each LED and throughout the entire probe is a highly desirable condition. The image processing can be calibrated for a non-uniform illumination, provided that the non-uniformity is stable over time, but that can require significant extra processing power and processing time. In addition, one or more light sources could be provided for emitting multiple wavelengths of light which can be used to provide different imaging results. The system could be tailored to provide for user selected changes in the wavelengths or could automatically cycle through the different wavelengths with the software adjusting the calculations based on the particular wavelength.

Figure 4:
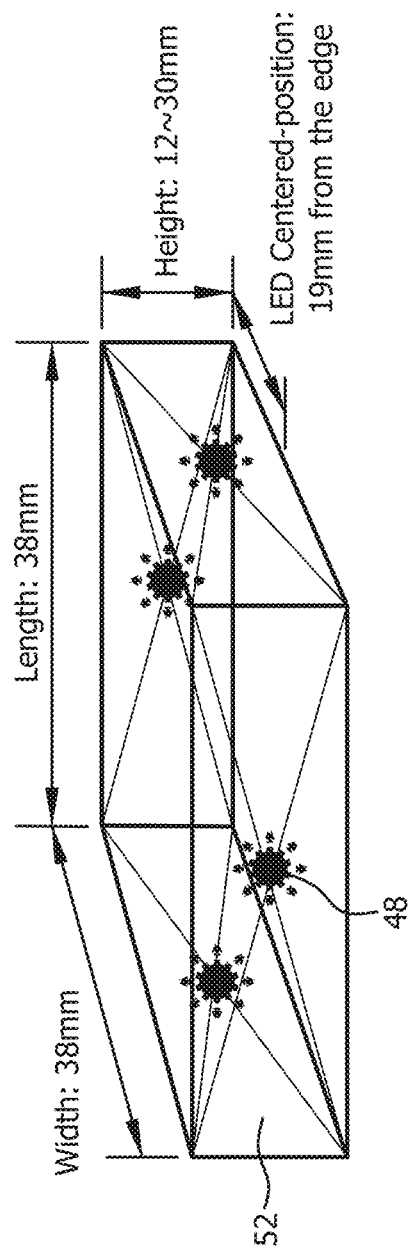
FIG. 4 is a diagram showing a possible position of LEDs for one embodiment of an elastomeric sensing element.

Referring now also to FIG. 4, one possible embodiment of the rectangular elastomeric element 52 is a block of PDMS 38 mm (1.5 inches) square, and between 12 and 30 mm (0.5 to 1.2 inches) thick. Four LEDs 48 are provided, one in the center of each narrow face of the block of PDMS 52 (approximately 19 mm from the corner edges). The number of LEDs 48 for each side can be increased in order to increase the area of illumination and/or the uniformity of illumination inside the PDMS. Often times the probe is covered with nitrile for sterilization reasons.

Alternatively, diffusing elements such as a white tube with the light source(s) inside it may be used to distribute the light uniformly within the PDMS. Other diffusing barriers can be used to generate uniform light into the sensing probe. Filters could be added between the light source and the sensing probe to tailor the wavelength of light that is channeled into the sensing probe.

Figure 5C:
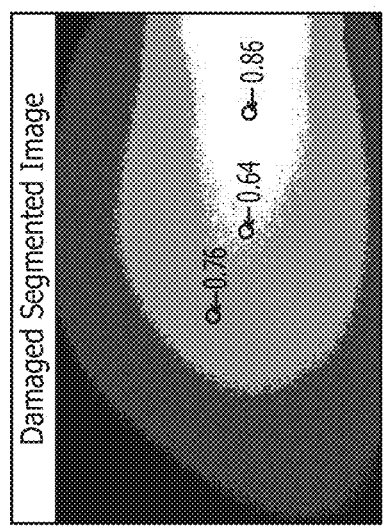
FIGS. 5A to 5C show images from the sensor under test conditions.
Figure 5B:
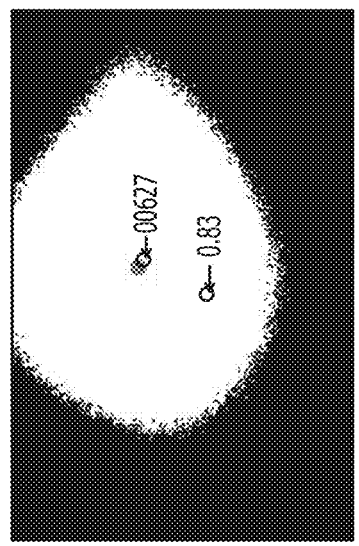
Figure 5A:
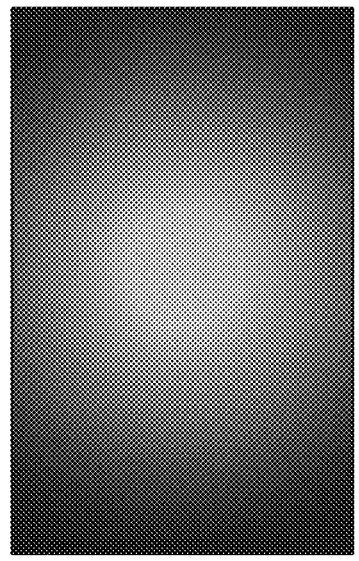

The light source alignment is important for the Compression Sensing Probe if good images that do not need a lot of post-processing are to be obtained. Under no load or deformation, theoretically, total internal reflection should not allow any light to escape, but because of impurities in the elastomer and because of the range of angles of the light injected into the elastomers, some light escapes the elastomer even when nothing is touching the surface of the elastomer. That low intensity light is found to form interference images. When the light sources are properly aligned and balanced, the interference images typically form concentric circles, as shown in FIG. 5A. When a light source is not aligned properly, the interference image becomes skewed and asymmetric.

In order to calibrate the light sources, compression-induced images are obtained. Those typically form a patch of light, brightest in the middle, that can be represented as a grayscale. Then the grayscale is segmented into black background and white image, and optionally also one or more intermediate (gray) rings, using available methods such as Otsu's threshold, as shown in FIG. 5B. Then the center of the segmented image is determined. Then the center of the image is moved by adjusting the light source illumination directions until it is at or near the center of the probe. For example, in Matlab software, the image may be approximated to an ellipse, and the "regionprops" function may be used to determine the center and the eccentricity of the ellipse. To measure the "roundness" of the region, the Matlab "regionprops" command also returns the eccentricity of the region, by specifying an ellipse and calculating the ratio of the distance between the focus of the ellipse and its major axis length. If the region is a circle the eccentricity value is zero and if it is a line the value will be one. The small circles in FIG. 5B represent the centroids of the layers (except for the background). The eccentricity of the central (white) segment is 0.0066, of the inner (lighter gray) ring is 0.27, and of the outer (darker gray) ring is 0.83. As may be seen from FIG. 5B, the two inner regions are quite well centered. FIG. 5C shows three small circles marking the centers of the background (black), outer ring (darker gray), and inner ring (lighter gray) regions, with eccentricities of 0.76, 0.64, and 0.86, in order from left to right.

If the image is evenly segmented into three regions, as shown in FIGS. 5B and 5C, region centroids and eccentricity scores can be calculated for each region. For the aligned image, the eccentricity scores and centroid locations are very close for the two inner regions. A proposed method for minimizing uneven interference and therefore aligning the LEDs is to adjust their position in order to produce a three segmented image with centroids close to the center of the PDMS area, with an eccentricity score below a maximum acceptable level. This level will be found experimentally, by comparing the quality of the alignment with the accuracy of the inclusion size estimation. LED adjustment will be mainly tilting the LEDs within their light tubes or moving them closer to or further from the PDMS. The light sources are then adjusted to obtain circular, uniform compression-induced images.

This method can be used to detect damage to the sensing probe 36. If, without any load, the image is severely asymmetric as shown in FIG. 5C, we suspect damage to the probe elastomer 46, such as a cut or crack. We can use this method to detect damaged probe (elastomer). Consistent deformation of the PDMS when the probe is applied to stiff objects is required for the image processing to estimate the object stiffness. The PDMS undergoes multiple forms of stress and strain during routine use. The material can eventually fatigue, and tears develop along the material. A tear is defined as a continuous separation of the PDMS, allowing air to enter the PDMS. Tears can be characterized by length across the surface of the PDMS, and depth through a cross section of the PDMS.

In FIG. 5C, the damaged PDMS produces an image with a bright spot near the edge of the PDMS. That causes the centroids of distinct regions to stray very far from center, as well as producing higher eccentricity scores due to the oblong shapes. If these two values are sufficiently off, the PDMS can be identified by the image analysis software as misaligned or damaged, and the user can be prompted by the software to remove the sanitary cover and inspect the sensing probe for LED misalignment or PDMS damage.

The overall intensity of the image changes in dependence on the lighting from the LEDs and on the ambient light. A threshold for the overall image brightness will be set to avoid frequent false positives.

Figure 6:
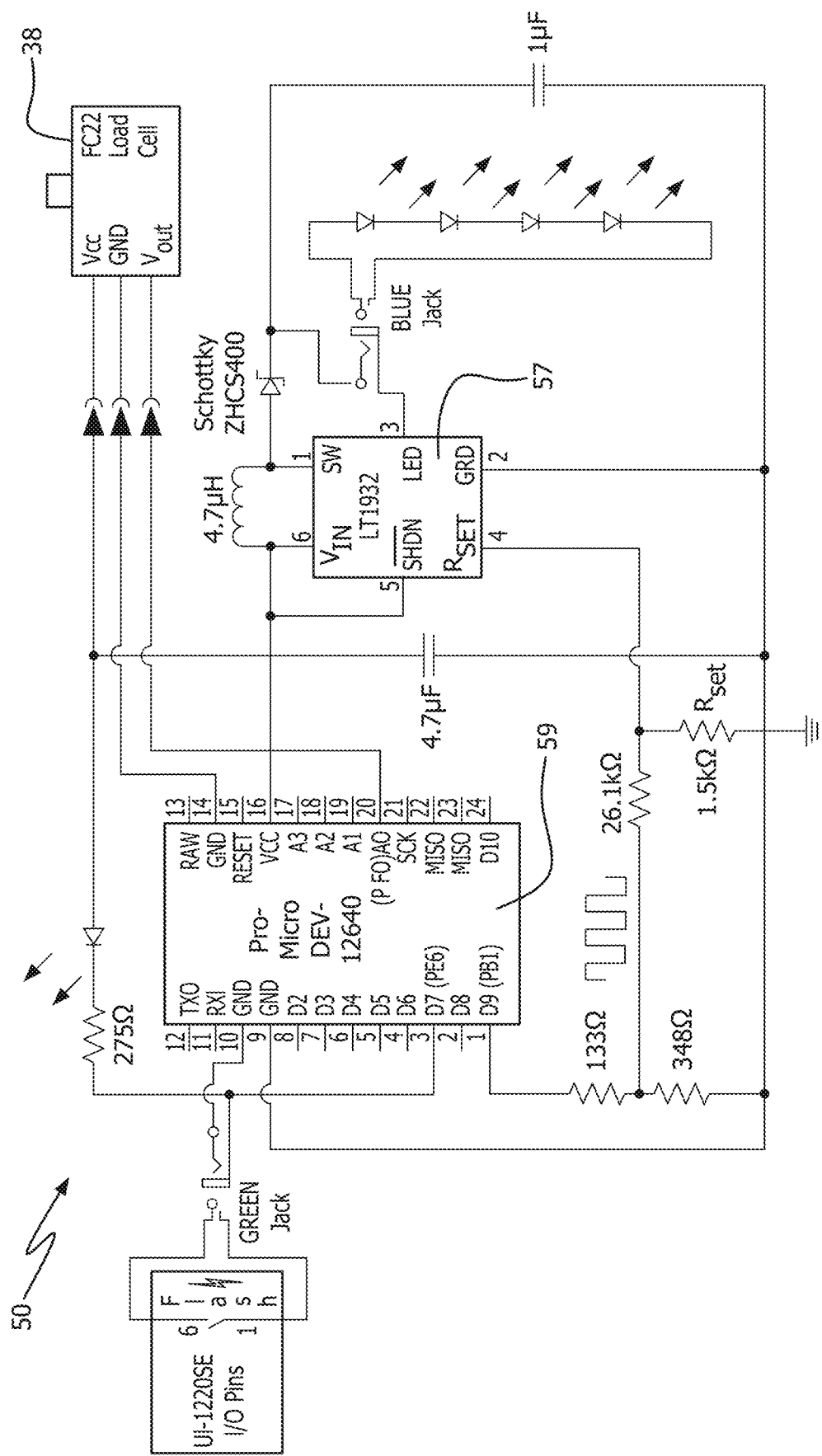
FIG. 6 is a circuit diagram.

Referring now also to FIG. 6, the primary purpose of the constant current driver circuit 50 is to provide constant current so that the light sources provide uniform luminosity even if a natural voltage dip occurs, for example, because the power unit 40 relies on batteries and the batteries are running low. One such circuit 50 is shown in FIG. 6 and uses a Linear Technologies LT1932 LED driver 57, controlled from a SparkFun Electronics DEV-12640 Pro Micro development board 59 with an Arduino processor. The Pro Micro 59 also receives input from the force measurement unit 38, which is a TE Connectivity FC22 load cell. The LED circuit was designed to give the user the ability to control the LED light intensity through a dimming option. As shown in FIG. 6, the Pro Micro 59 also has a jack for input from an image sensor (IDS Imaging Development Systems GmbH UI-1220SE) in case for any reason it is preferred to use a dedicated imager on the frontend attachment 24 instead of the camera 32 on the smartphone 22. In the illustrated embodiment, the Arduino processor includes a Bluetooth transceiver. Alternatively, a separate Bluetooth transceiver may be provided.

The applied force can be measured by one or multiple force sensors 38 in the frontend attachment 24. This force sensor 38 can be a pressure sensor, load cell, strain sensor, piezoelectric sensor, strain gauge, etc. The direction of the applied force is important. The frontend 24 or the mobile device 22 can have attitude and position sensors to determine the applied force direction in absolute terms. More accurate results will be obtained if the applied force direction is measured by various sensors 38, so that the direction of the applied force relative to the device 20, and in particular any unevenness in the applied pressure, can be detected.

One possible embodiment is an FC22 compression load cell with perpendicular application of the pressure. The FC22 uses micro-machined silicon piezoresistive strain gauges (Measurement Specialties, 2012). The FC22 measures direct force, which is more reliable than alternative sensors that measure force by a pressure capsule. Because the FC22 series incorporates micro fused technology, it eliminates age-sensitive organic epoxies, which provides an excellent long-range span and essentially unlimited cycle life expectancy. The exemplary FC22 force sensor or applied force measurement unit 38 will be integrated into the frame of the frontend attachment 24, which then creates a stable platform to take force measurements. To increase the accuracy of the analog force sensor data, a buffer can be used to store multiple values of the force sensor, which can then be averaged.

The force sensor 38 is connected to a processor 44 such as the exemplary Pro Micro microcontroller 59. The force data will be synchronized with the CIS image. In an embodiment, the Bluetooth-enabled microprocessor 59 is connected to the force sensor 38. When the take image command is generated on the smartphone 22, the smartphone 22 sends the command to take CIS image to the smartphone camera 32, and sends a Bluetooth command to the microprocessor 59 to obtain applied force information from the force sensor 38. Then the force data is sent by Bluetooth to the software unit 34 of the smartphone 22, where the force data is written into the CIS image metadata. It is also possible to have a hardware trigger from the smartphone 22 to the microcontroller 59. A hardware trigger will lead to more accurate force/image synchronization.

The processing unit 44 has three main functions, obtaining and converting the raw force sensor data into usable force information, reading light brightness values, and controlling the light brightness. This processing unit can be a microprocessor, a FPGA, or a computer.

One possible embodiment of the brightness control is done by the application software 34 in the mobile device 22. The dimming functionality can be controlled by varying the output of a PWM signal from 0-255 in increments of 30, where 0 is low, and 255 is high. It is also contemplated that the processor 34 of the smartphone 22 can be used as the microprocessor 59, with a software app on the phone 22 programmed to receive the force sensor data and brightness data and for controlling the brightness.

Figure 8:
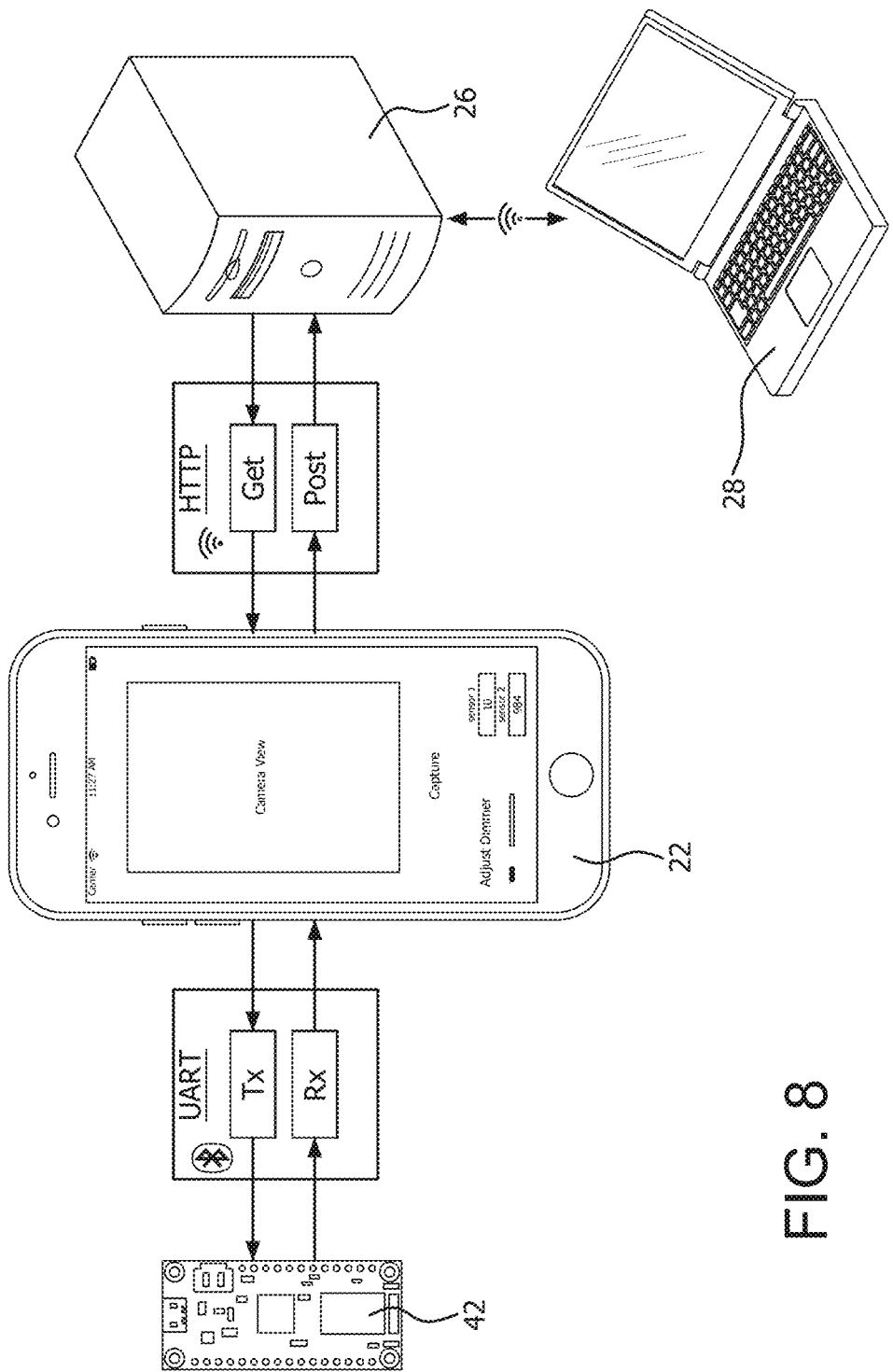
FIG. 8 is a diagram of communication flows.

Referring now also to FIG. 8, the main function of the communication unit 42 is to provide the useful data to the mobile device 22 and obtain commands from the mobile device 22. This can be a wireless communication such as Bluetooth or Wi-Fi, or it can be a wired connection between the frontend attachment 24 and the mobile device 22. One possible embodiment is Bluetooth connection between the microcontroller 59 of the frontend attachment 24 and the processor 34 of the smartphone 22, then Wi-Fi HTTP or HTTPS connection between the smartphone 22, and particularly its communication unit 30, and the cloud server 26.

The initial communication begins with the microcontroller 59 in the frontend attachment 24 and the smartphone 22 connecting via Bluetooth Smart connection. There are two main components in the Bluetooth connection: they are the peripheral and central. In this embodiment, the smartphone 22 is the central, and the microcontroller 59 is the peripheral: this is similar to a client and server relationship.

Unconnected peripherals advertise data such as their name, signal strength, and universally unique identifier (UUID). Once connected, peripherals will share their services; the service that will be used is the universal asynchronous receiver/transmitter service. It essentially acts as the data pipe between the microcontroller 59 and smartphone 22. The service has two characteristics, "Tx" and "Rx", this is what will be used to transfer force data and control the dimming. Suitable secure protocols to make sure that the smartphone 22 connects to the correct front end unit 24, and to avoid external interference with, or interception of, the wireless transmissions are well known, and in the interest of conciseness are not further described here.

To use this method, an instruction set is created to handle the different functions needed to obtain the force data from the force sensor 38 and control the dimming of the LEDs 48.

The communication between the smartphone 22 and the cloud server 26 (which in this embodiment is running PHP scripts) will be through Wi-Fi if available. The image is sent in, for example, JPEG format and the pertinent data is sent in a JSON file using the HTTP post method. To retrieve data from the cloud server 26, the smartphone app 34 will use the HTTP request method. By using JSON files, the data is parsed in a way that makes retrieving information simple. With communication established, the software must ensure that messages are the same "language": in the embodiment, all data passed between the platforms conforms to UTF-8 string encoding.

The power unit 40 provides all the necessary power to the frontend attachment 24. That will include the light source(s) 48, constant current driver 50, force sensor 38, processing unit 44, and communication unit 42. The power unit 40 can be a battery or a fuel cell.

Where the mobile device 22 is a smartphone, the camera, video camera, accelerometers, gyroscopes, and communications hardware available in a typical smartphone can be utilized, in particular the camera 32, application software 34, and communication unit 30. One possible embodiment is an iPhone. iPhone 6 has an 8 megapixel with 1.5 μm pixels video camera, accelerometer, gyro, and compass, Wi-Fi 802.11.

Figure 7:
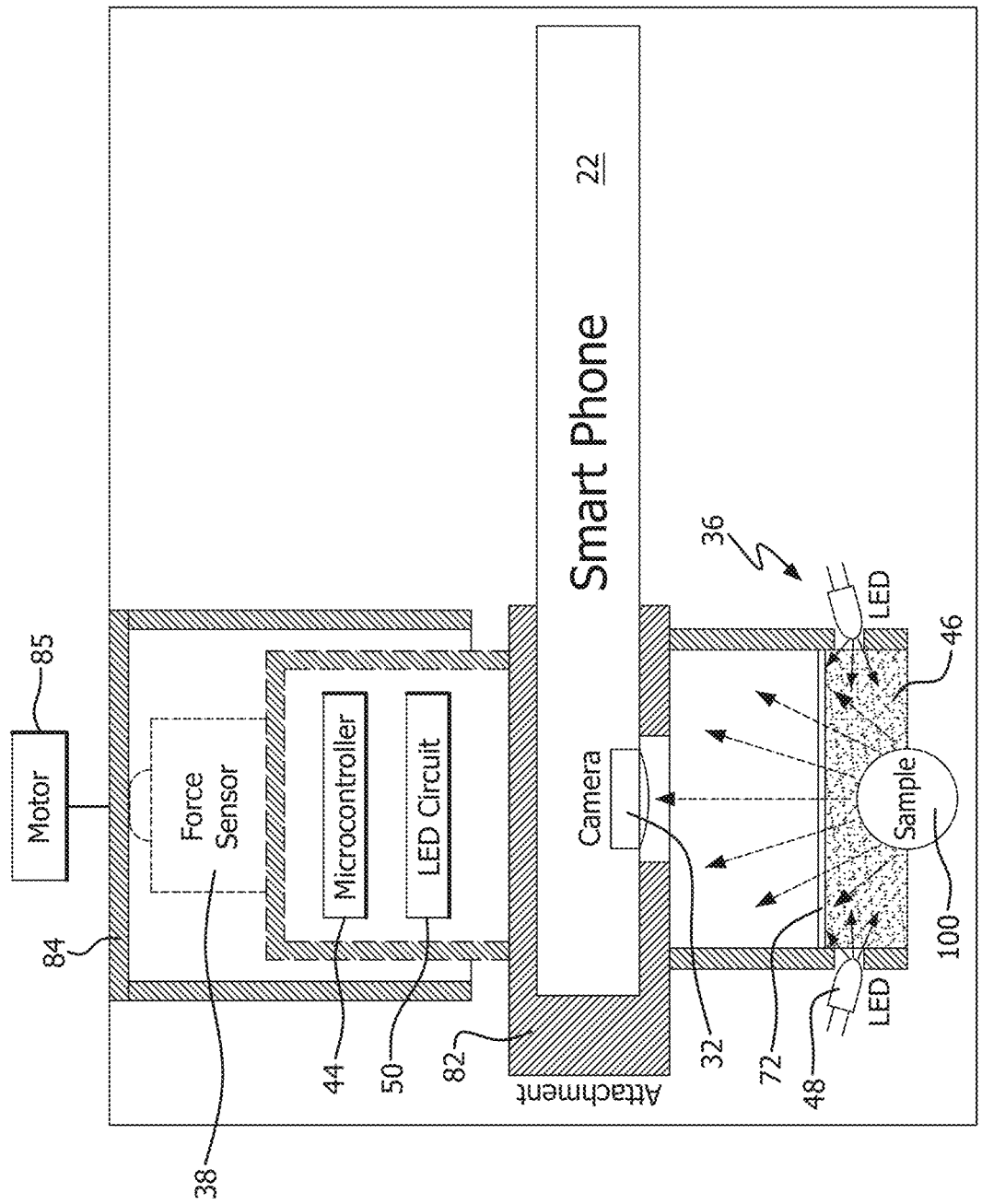
FIG. 7 is a schematic side view of the mobile-platform CIS.

As may be seen from FIG. 7, the camera 32 views the elastomer 46. The frontend attachment 24 is designed in such a way that the elastomer 46 is visible from the mobile device camera 32. The camera 32 is able to focus at the edge (side) of the elastomer 46. The camera's autofocus is deactivated and the focal distance is set in software or firmware. For each combination of camera model and front-end device model, the focal distance is fixed, so can be pre-programmed. The camera 32 captures the light escaping from the elastomer 46 as the elastomer 46 is compressed and distorted by the target object. The camera 32 can capture a single image, multiple still images, or one or more video images.

The main function of the application software 34 is to obtain CIS image data along with the metadata such as the applied force from the force sensor 38, user number, case number, date, time, and dimming value, and send this information to the cloud server 26. The data is encrypted and compressed in this application software 34. Also, the application software 34 will receive the malignancy score and other output information returned from the local processing unit 28.

The mobile device's built in wireless communication function is used to send obtained data and receive the results. This communication can be via Wi-Fi, LTE, 3G, or Bluetooth. Other ftp or http sockets can also be used.

The compression-induced images that are obtained from the CIS imager are sent over Wi-Fi to the remote cloud server 26 or local computer 28, which runs mechanical property estimation algorithms. The obtained images with corresponding histopathology results are stored in the cloud database. This database is used to compute the malignancy score. That allows the server 26 to keep a comprehensive database for more accurate performance evaluations. Therefore, the communication should be secure. To achieve efficient and secure communication between two entities, symmetric encryption-based communication schemes are often adopted. Either symmetric or asymmetric encryption may be used to secure the data.

For symmetric encryption, secret keys are often transmitted with the help of asymmetric encryption methods, which need the support of public key infrastructure. Asymmetric encryption, even if only of the keys, causes considerable computation and communication overhead for the CIS. What is worse, if there is any risk that the secret key has been compromised, the CIS has to generate another secret key, and transmit it with the costly asymmetric encryption method.

To overcome these problems, the present embodiment uses a different secure communication protocol. The proposed communication protocol is reasonably secure without introducing the public key infrastructure. Additionally, the secret key is generated in a very efficient way. Specifically, during the initialization process, there is no secret key shared between the smartphone 22 and the cloud server 26. Instead, the smartphone 22 and the cloud server 26 randomly chat with each other using plaintext, without sending any sensitive or secret information. After several rounds of interaction, both the smartphone 22 and the cloud server 26 generate a secret key using a hash value of their chatting contents. In order to generate the same secret key, an attacker must intercept all the plaintext in the chat. Fortunately, there is often serious packet loss in wireless communication, so it is very hard for an attacker to get all the chatting contents. If the chatting entities cannot hear each other clearly, they can ask to repeat the message. An eavesdropper cannot do that. The robustness of the security is based on the lack of robustness (characteristics of packet loss) of the wireless communication. In this way, the secret key is generated without introducing the public key infrastructure. To make the communication more secure, after each successful communication, both entities update their secret keys. Therefore, even if the attacker steals a secret key, it will soon expire, and as soon as the attacker misses a data packet, the attacker will no longer be able to match any future key update.

The CIS data can be sent to the local processing unit 28 directly or through the cloud service 26. It is preferred that the CIS unit 20 connects to the cloud server 26, and then the local processing unit 28 obtains the data from the cloud server 26. In the cloud, one can store encrypted compression-induced images with metadata. The mobile device 22 and the local processing unit 28 communicate with this cloud server 26. The cloud server database stores the data and metadata until it is ready for data processing on the local computer 28.

One embodiment of the cloud server 26 acts as a repository for all of the data and has two main components, the PHP scripts and a MySQL database. There are two PHP scripts: one receives the data sent from the smartphone 22 and stores them in the proper directories; the second goes to the proper directory and returns result information back to the smartphone 22.

The local processing unit 28 obtains the CIS data and processes the data to obtain the mechanical property information. The CIS data and metadata are stored and processed in this computer 28. This local processing unit 28 can be in the cloud 26, but in the present embodiment the local processing unit 28 is in the responsible medical practitioner's own location for security purposes. Thus, the data in the cloud 26 is never unencrypted. The processed data is then returned to the originating mobile device 22. The user of the system is then able to obtain the desired information on the mobile device screen.

Figure 9C:
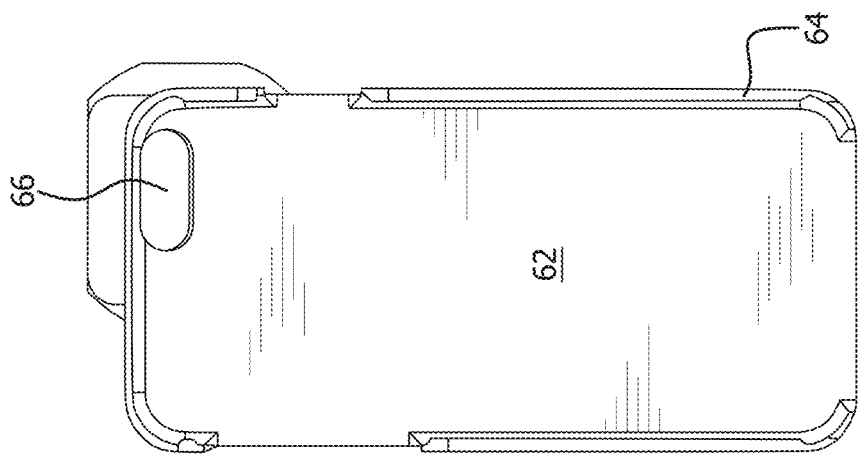
FIGS. 9A, 9B, and 9C are front, side, and back views of a frame forming part of one embodiment of a CIS.
Figure 9B:
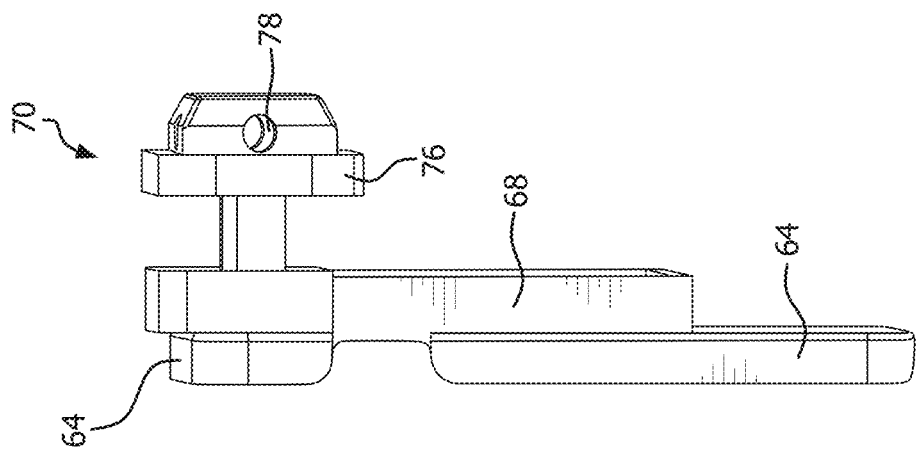
Figure 9A:
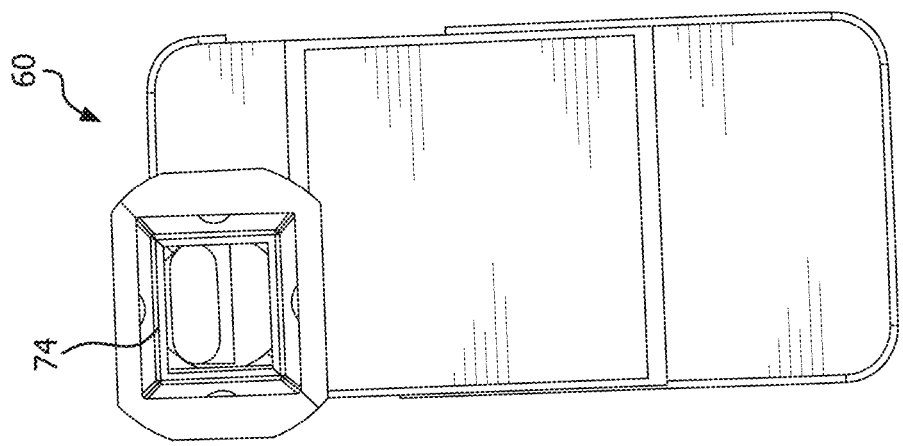

Referring now also to FIGS. 9A, 9B, and 9C, collectively FIG. 9, one embodiment of the mobile-platform compression-induced imaging system 20 comprises a frame 60. The purpose of the frame 60 is to hold the frontend 24 and let it seamlessly attach to the mobile device 22. The elastomer element 46 of the sensing probe 36 is visible to the imaging unit 32 of the mobile device 22. The force sensor 38 is positioned to obtain accurate applied force information.

The frame 60 comprises a cradle 62 with raised sides 64, onto which the smartphone 22 can be placed, with the camera 32 aligned with an aperture 66. Accordingly, here the frame 60 and cradle 62 define the receptacle into which the mobile device 22 may be received. If the smartphone 22 has an autofocus sensor next to the camera 32, the aperture 66 may be elongated, as shown, so that the camera can focus on a target at the edge of the sensing probe 36. Alternatively, the autofocus may be overridden in software, and the camera 32 forced to a known focus setting.

The frame 60 shown in FIG. 9 was designed for an Apple iPhone 6, but many other available models of smartphone 22 have a similar general configuration and would require at most a slight modification of the dimensions of the cradle 62. The frame 60 shown was created in SolidWorks CAD software and printed using an Objet 3D printer.

The frontend attachment frame 60 is the skeleton for the system in that it contains all the LED circuit 50, PDMS probe 36, force sensor 38, and smartphone 22, and holds them in alignment. The goal of this design is to create a lightweight, easy to hold device that can accurately capture the tactile image and force sensing information.

The cradle 62 firmly holds the smartphone in place to allow for a certain pressure to be applied on the phone without the phone moving or damaging any parts. The cradle 62 does not interfere with the view of the camera or smartphone screen or access to any of the buttons so that full phone functionality is maintained. If wired communication is used between the smartphone 22 and the frontend processor 59, the cradle 62 may have a connector plug that fits into a port in the smartphone 22 when the smartphone 22 is inserted into the cradle 62. The cradle 62 is used here as a handle for a user to hold the CIS assembly 22, 24 and to press the sensor 36 and particularly the elastomer 46 against the target.

Directly beneath the smartphone cradle 62 is a storage compartment 68 for the electrical components. The size of the compartment 68 is set to contain the microcontroller 59, battery pack 40, power switch, LED driver 50, force sensor circuitry, and some wiring. For protection and aesthetics, the compartment 68 is enclosed by a lid, but has external access points for the power switch and wiring essential for the LEDs and force sensors.

At the front side of the frame 60 is an area 70 for the image capture. The hole 66 for the camera 32 is central with the location of the camera 32 on the smartphone 22 itself. The distance from the camera 32 to the sensor elastomer 46 is selected to be within the focal range of the camera 32, which in the embodiment of FIG. 9 was provided by the manufacturer to be 31 mm minimum. An additional lens (not shown) can be added in front of the smartphone camera 32 to reduce the minimum focus distance or to capture the appropriate size image.

A glass or other rigid, transparent sheet 72 (see FIG. 7) may be incorporated between the elastomer 46 and the camera 32 as a rigid support for the elastomer 46. The glass/plastic 72 supports the back of the elastomer 46, while permitting the camera 32 to see through. The glass/plastic 72 and elastomer 46 are placed in a rectangular cutout 74 in a holder 76 at the front end of the frame 60, and the elastomer 46 fits securely in that cutout against the glass/plastic 72. Four holes 78 symmetrically placed in the holder 76 around the cutout 74 are the access points for the LEDs 48. The LEDs 48 are secured within metal spacers lining the holes 78. All wiring for the LEDs is channeled away from the imaging area and is arranged with wires that are as few and as small as reasonably practical, so that the holder 76 can freely move. It is also contemplated that the rigid support for the elastomer 46 could be provided by the holder 76 which surrounds the perimeter of the elastomer 46.

In the embodiment of FIG. 9, the applied force is estimated from the accelerometers and gyroscopes of the smartphone 22. Alternatively, or in addition, it is possible to put a thin force sensor on the frame 60 where it touches the tissues at the edge of the elastomer 46.

Figure 10B:
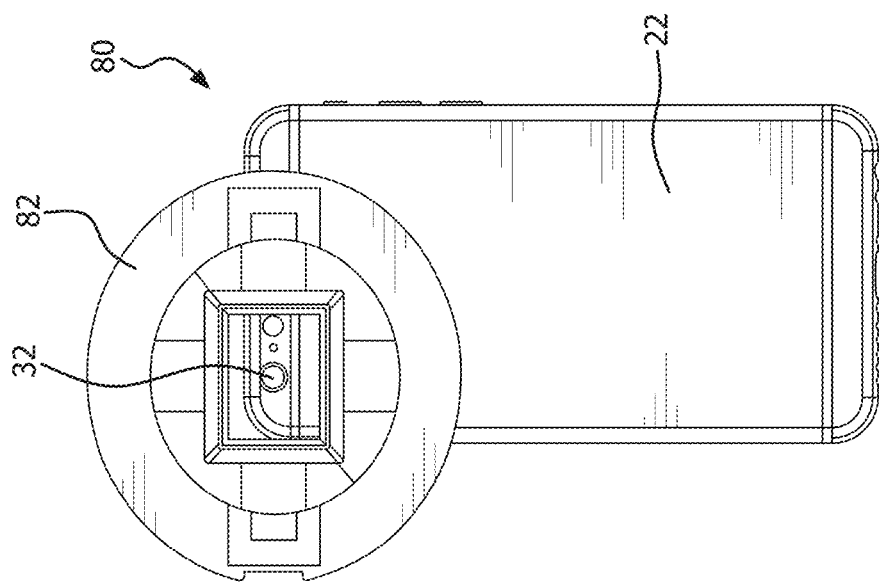
FIGS. 10A and 10B are perspective and front views of another frame forming part of an embodiment of a CIS.
Figure 10A:
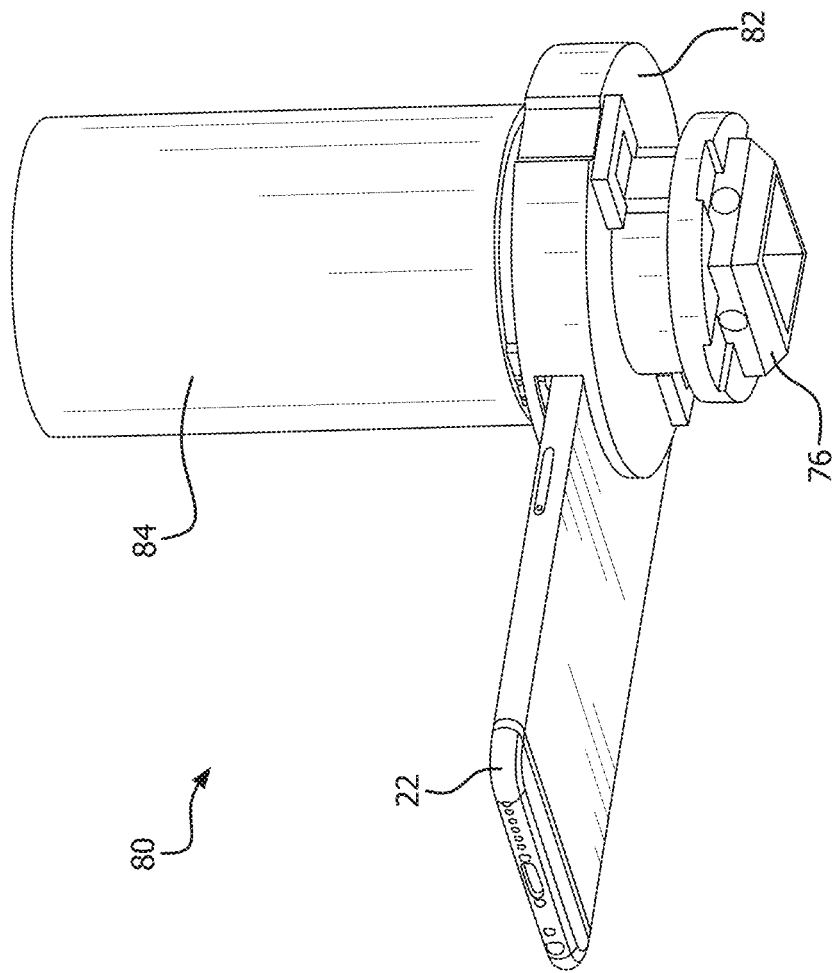

Referring now also to FIGS. 10A and 10B, collectively FIG. 10, and to FIG. 7, a second embodiment of frame 80 is similar in principle to the first embodiment, and the description will not be unnecessarily repeated. In the frame 80, the corner of the smartphone 22 that includes the camera 32 is inserted into a slot in a cradle 82. Once again, the frame 80 and cradle 82 define the receptacle for holding the mobile device or smartphone 22. A housing 84, behind the cradle 82 and aligned with the holder 76 for the elastomer sensor 46, contains all the electronics and is used as a handle. The housing 84 is not rigidly attached to the cradle 82. Instead, they are connected through the force sensor 38, so that when a user holding the housing 84 presses the sensor 36 and particularly the elastomer 46 against a solid object, the force sensor 38 detects and measures the force applied to the handle here again in the form of the housing 84. In the interest of simplicity only a single force sensor 38 is shown in FIG. 7, but as mentioned above, multiple force sensors may be used to increase accuracy, and to detect any unevenness in the applied pressure.

Figure 11:
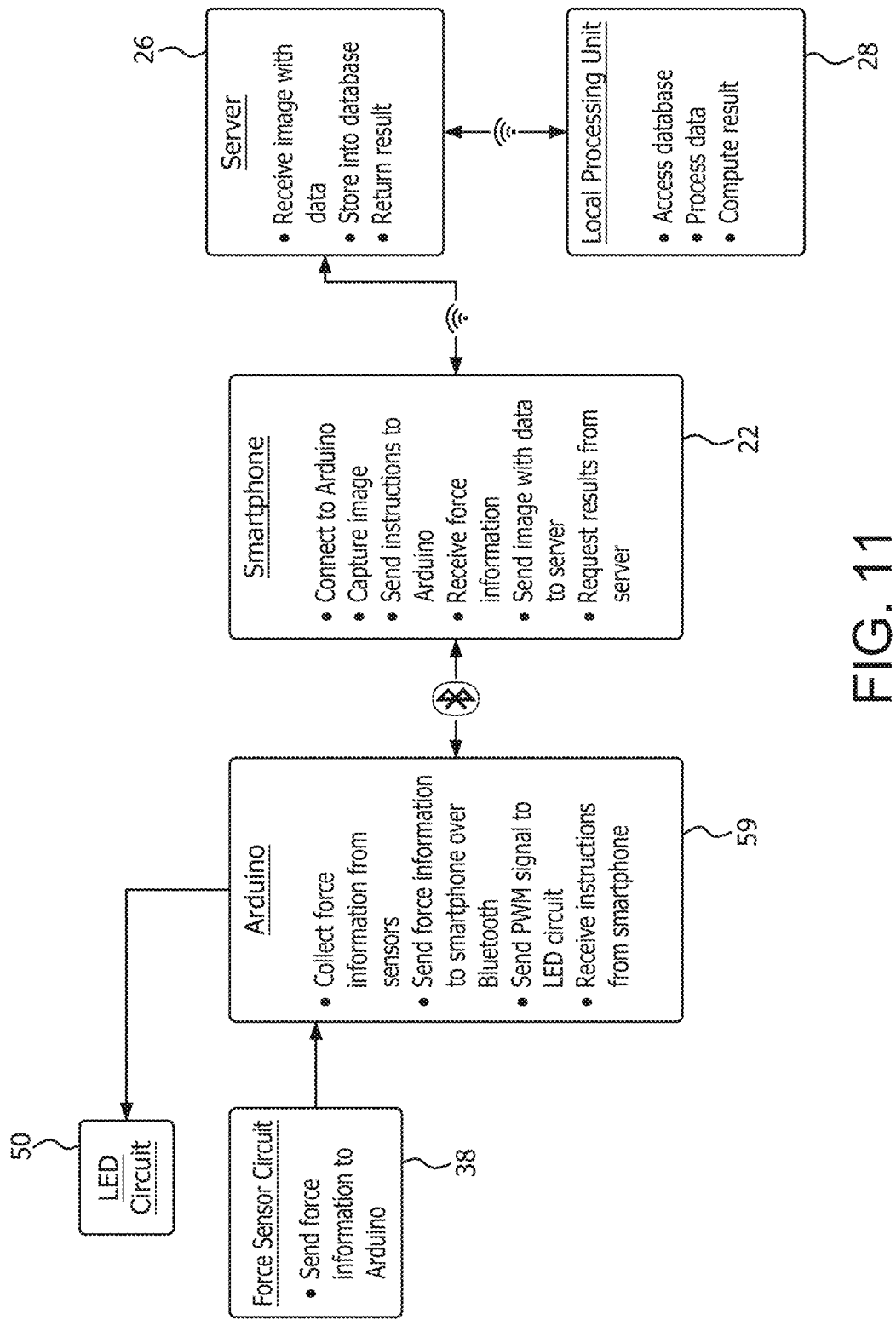
FIG. 11 is a functional block diagram of an implementation of a method of data transfer.

Referring now also to FIG. 11, in order to determine the mechanical properties of the target 100 it is necessary to obtain data from the frontend attachment 24 and mobile device 22. An embodiment of the method of data collection is implemented in three main hardware components: the microcontroller 59 of the frontend attachment 24, the mobile device (e.g., smartphone) 22, and the local processing unit 28. The method is responsible for acquisition of data, processing of CIS data, and communication between hardware.

While the above embodiment describes manually applying force, it is also contemplated as shown schematically in FIG. 7 that a motor 85, such as a linear actuator, screw drive, pulleys or timing belts, could be incorporated into any of the embodiments to automatically apply the desired force. For example, the motor 85 could be coupled between the housing 84, the cradle 82 or the holder/frontend 24 and a fixed or non-moving surface so as to, upon activation, drive the optical waveguide or the compression sensing probe 36 automatically towards the target 100. This will allow automatic force application instead of pressing manually. In one application, the motor 85 drives the optical waveguide 46 toward the target area 100 in a uniform motion of about 5 to 7 mm in approximately three seconds to obtain the tactile images.

In the frontend attachment 24, the processor 59 obtains the force sensor data and transmits it to the mobile device 22. The processor 59 also controls the brightness of the lighting and communicates with the mobile device 22. As an embodiment, the method can be programmed in C using an Arduino IDE microprocessor 59. An example of the functions of each component is shown in FIG. 11.

Figure 12:
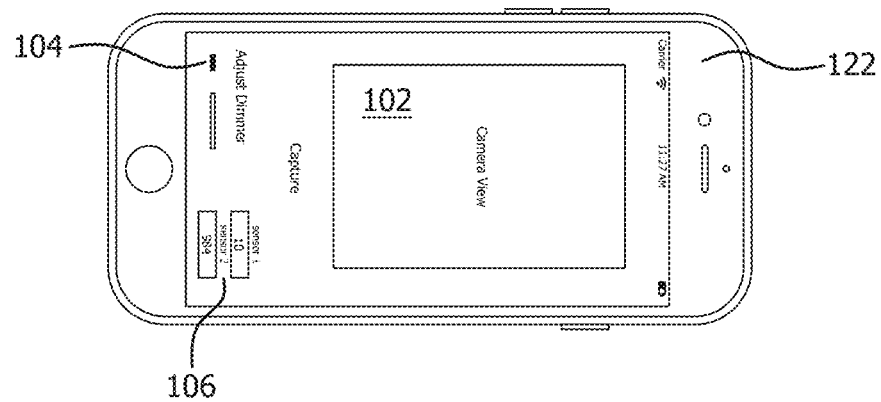
FIG. 12 shows a user interface on a smartphone.

The mobile device unit 22 gathers CIS images and applied force data, sends instructions to the frontend processor, and sends CIS images and related data to and requests results from the local processing unit 28. One possible embodiment of the data acquisition method is iOS application software. Referring to FIG. 12, the software interface on the display screen of the smartphone 22 provides a live camera view 102 of the probe 36, a slider 104 to adjust the brightness of the LEDs 48, fields to add patient information, a display 106 for force readings, and lastly a button for the user to capture the photos. Once the capture button is pressed, the captured photo is displayed on the screen and the user is given the option to either upload the photo or retake it. It is also possible to take video images. The images are correlated with the applied force information from the force sensor 38.

Figure 13:
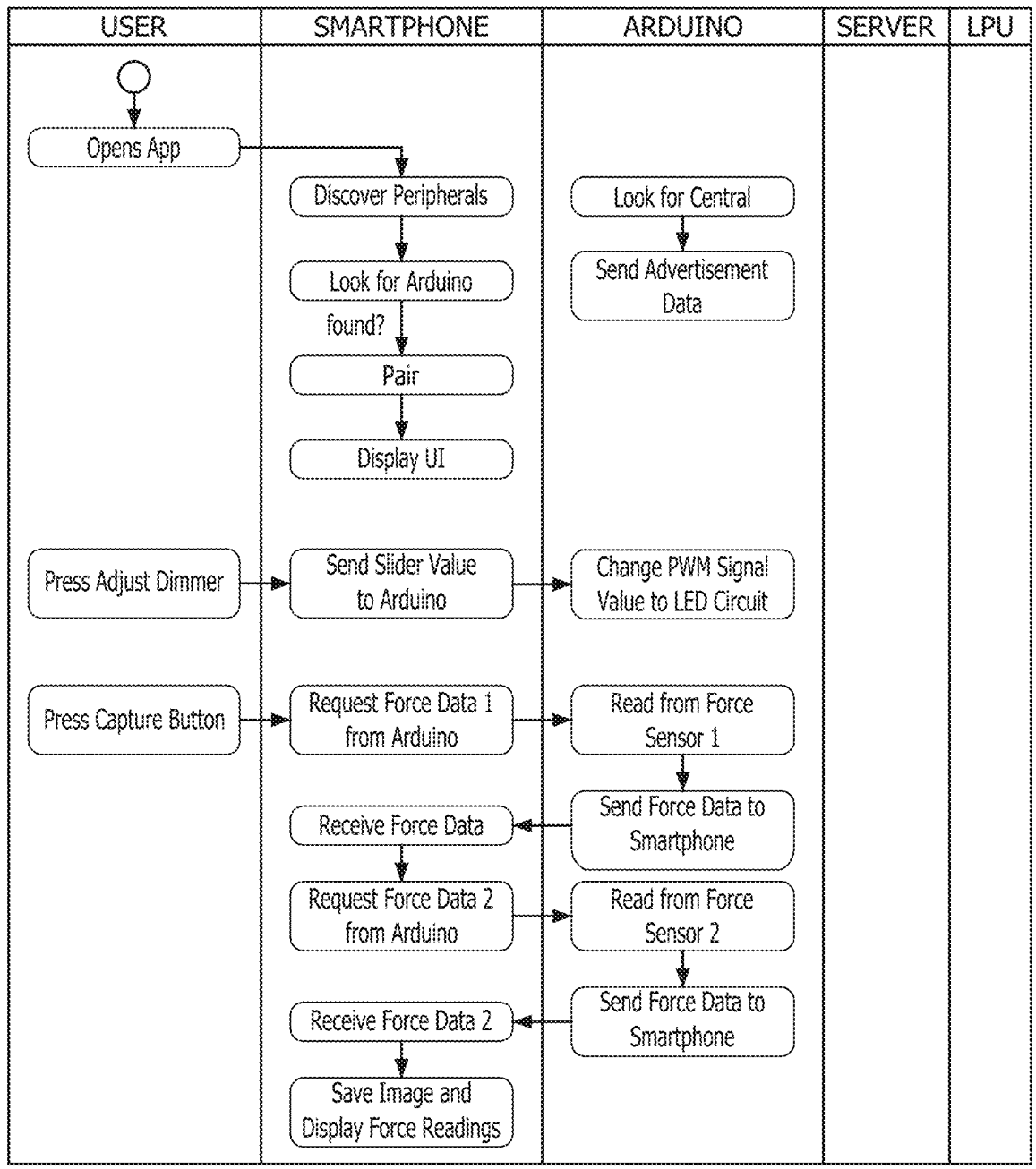
FIG. 13 is a diagram of data acquisition flow between a mobile device and a front end microprocessor.

The application software 34 in the smartphone 22 captures the CIS images, force data, and metadata. Referring to FIG. 13, in one possible embodiment of the data acquisition process, when the operator presses the capture button, the sequence of data collection begins by sending a command over Bluetooth to the frontend microprocessor 59 requesting the force information. The frontend microprocessor 59 reads and stores the current force value. The current force value may be a single value, an average of values from two or more sensors, or a list of values from two or more sensors. In FIGS. 12 and 13, two force sensors 38 report separately. Because the programs run asynchronously, the stored values are sent one at a time to prevent errors caused during transmission. Meanwhile the application software on smartphone 22 continues and collects an image using camera 32. Once the applied force information is returned to the smartphone 22, the captured image and the force data are displayed on the smartphone 22. The user is then prompted to either retake the image or upload it.

Figure 14:
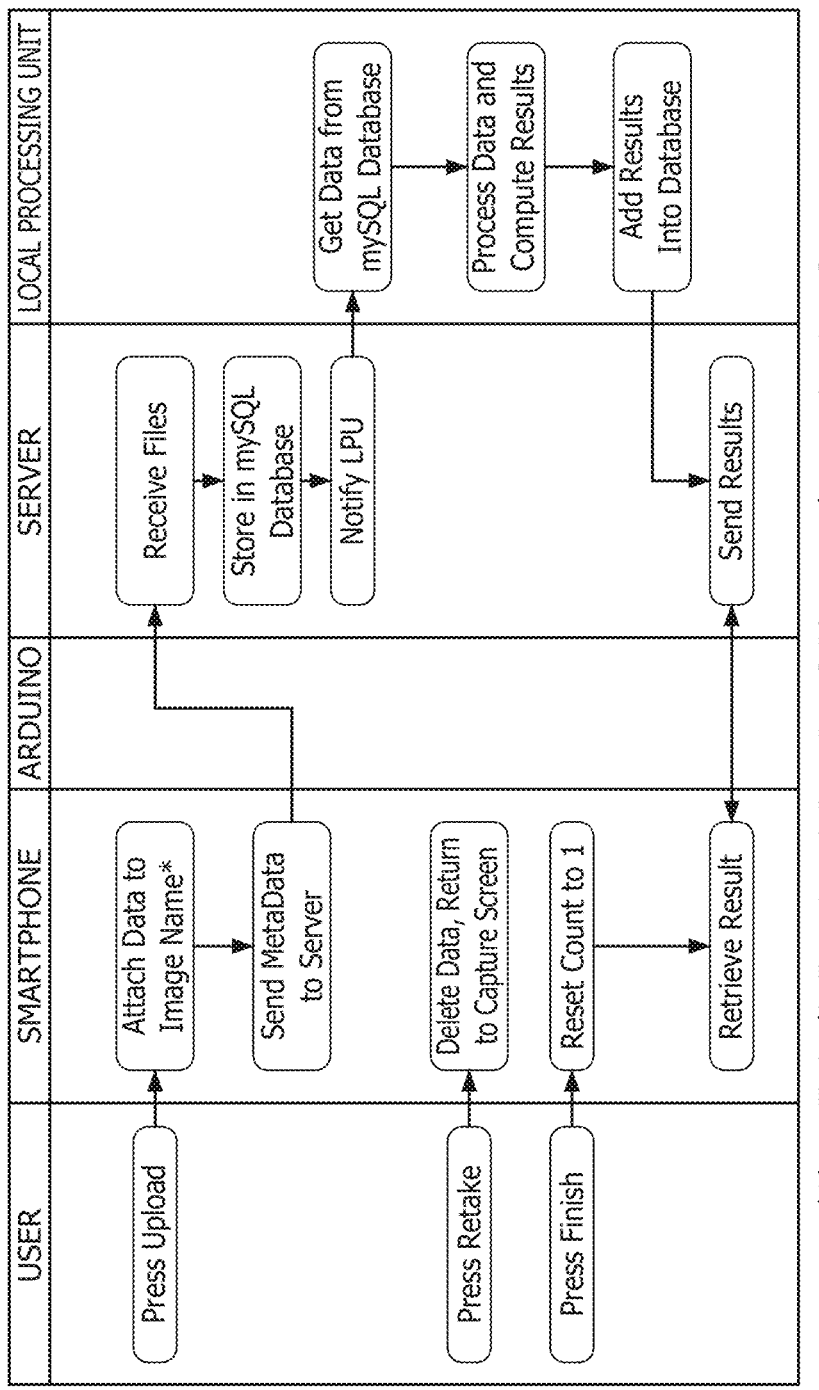
FIG. 14 is a flow chart for interface between the mobile device, a server, and a processing unit.

When the user selects an upload button, the connection to the server begins. The file including the images and metadata is prepared. The metadata may contain any or all of the date, time, dimmer value, patient ID, and User ID, and the force information. These data may be used to form the image name, in a format by which the data can usefully be sorted. FIG. 14 shows an example of the data flows in uploading the data.

Where it is desired to capture multiple images at different applied forces, the smartphone 22 may record a segment of video, while repeatedly polling the frontend 24 for force data. The force data is then analyzed to find a period when the rate of change of force with time is relatively uniform, and a portion of video, or two or more individual frames at a desired spacing of time or force, is selected for further analysis. If the smartphone 22 has sufficient processing power, the selection may be performed, and the selected frames presented for approval by the user, before uploading. If the smartphone 22 does not have sufficient processing power to perform the selection, the unselected data can be uploaded and selection performed at the local computer 28, but at greater expense in communication usage.

Size Determination Method with Mobile-Platform CIS Using 3D Interpolation

One of the mechanical properties that Mobile-platform CIS determines is the size of the target 100. Here, we describe a method to obtain the size of the subsurface or surface targets.

In order to choose the optimal CIS images, force is plotted versus time. A smooth linear region is chosen to process the images. These images are used in a mechanical property estimation algorithm. It is desirable to filter out noise from the CIS images. The noise may be due to, for example, spurious ambient light entering the system, or non-imaging light from the LEDs 48 if the position of the LEDs is not ideal. Maximum intensity and/or sum of intensity of the CIS images are used to estimate the target size. The shape of inclusions is assumed in this embodiment to be spherical. A 3D interpolation model to estimate the size of tumors 100 from the compression-induced image is provided. The 3D interpolation method relates applied normal force, F, number of pixels on the compression-induced image, $N_p$, and the diameter of the inclusion image, D. We model the multiple surfaces based on these three parameters. Once we have the models, we obtain force F from Mobile-platform CIS, and the approximate depth from the user. Then, we use the model surface to estimate the size. We developed multiple 3D interpolation surfaces of the form shown in Equation (1) for a range of depth layers from the experimental data.

$$D(F, N_p) = \sum_{i=0}^{i=n}\sum_{j=0}^{j=m} p_{ij} F^i N_p^j \tag{1}$$

The model coefficients, $p_{ij}$, define the modeled surface. Indices n and m in Equation (1) denote the order of the polynomial for the size estimation. The coefficients $p_{ij}$ are empirically found from a model as described below.

One possible embodiment is to divide the size into two cases. We developed two sets of the 3D interpolations: one for large inclusions (e.g. we used two diameters, 11.9 mm and 15.5 mm, to generate the initial interpolation surfaces) and another for small inclusions (e.g. we used diameters of 8.0 mm and 9.9 mm to generate the initial interpolation surfaces). Thus, to decrease the error, we have two different interpolation surfaces: one for small inclusions and another for larger inclusions. The interpolation surfaces from each set were determined for three different depth layers (in this example, 3 mm, 6 mm, and 9 mm). The values of the developed 3D interpolation surfaces parameters reflect the depth and size changes in inclusions within the tissue phantom. It is possible for a doctor to qualitatively estimate the depth (shallow, medium, or deep) and size (large or small) of the tumor, so that the appropriate surfaces according to the doctor's description can be used.

Using the developed 3D interpolation surfaces, we can estimate size of the inclusion by specifying the applied force, F, and number of pixels on the image, $N_p$. The size of the inclusion is found from force information and number of pixels, using its approximated depth. We had multiple interpolation surfaces for different depths. The choice of a particular 3D interpolation surface is based on the approximated depth and size of the inclusions. For human data experiments, the physicians estimated approximate size and depth of the inclusions. Then more accurate size and depth are computed using this 3D interpolation method. Initial interpolation surfaces can be generated from the developed model, but as more data are gathered, a more accurate interpolation surfaces may be determined from the actual data.

Relative Softness Index Determination Method

The compression experiment of Mobile-platform CIS resembles in some respects a conventional tensile test to determine the mechanical properties of an inclusion. One of the properties that we consider is the softness index, which is the degree of softness/hardness of the target. In contrast to the rigid steel compression surface used in conventional hardness measurements, the present approach uses a soft silicone probe to compress the tissue with soft inclusions. The size and shape of the deformation of the silicone probe element of the Mobile-platform CIS give information about the tissue with an inclusion. However, the difference in compression surface stiffness influences the output of these two methods. In a conventional tensile experiment with a rigid probe, the sample deforms, and the deformation for a stiff sample/inclusion is smaller than for a soft inclusion. In the present measurement method, it is the deformation of a soft probe that is measured, and the deformation of the probe is larger for stiffer samples and smaller for softer samples. The softness index, Sass, that is obtained is the inverse of the elastic modulus.

Elasticity describes the ability of a tissue to recover its shape after an applied stress is removed. Human skin and soft tissue responses on compression, as well as responses of tumors, are examples of elastic tissue recovery. Also, biological tissues are non-linear and viscoelastic materials. We worked with the small range of the indentations (up to 20% of depth reached). In all Mobile-platform CIS experiments, we assumed the linear elastic behavior of the tested materials. We used the changes in the indentation of the soft silicone probe to capture the deformation of the tissue from compression. Then we estimated the tumor region's softness index, which is a relative tensile property measure.

The Mobile-platform CIS softness index calculation with a tissue phantom was designed to replace the conventional elastic modulus measurement technique using compression.

In the Mobile-platform CIS application, the stress $\sigma_z(k)$ for each CISS image k is calculated as follows, $$\sigma_z(k) = \frac{F(k) - F_{ref}}{A_C} \quad (2)$$

F(k) is the applied force in the z direction, $F_{ref}$ is the force value taken at the reference point. The reference force corresponds to the first non-empty tactile image during experiments. $A_C$ is Mobile-platform CIS contact area (e.g. 1134 mm$^2$), which includes the solid frame and the elastic silicone probe areas. It is assumed in this example that the entire front face of the probe, including the frame, is pressed flat against a flat surface of the medium containing the sample 100. If the landing surface is not flat, $A_C$ may be adjusted accordingly.

The vertical deformation ratio, $d_z(k)$, of Mobile-platform CIS is given as $$d_z(k) = \frac{|I(k) - I_{ref}|}{I_{ref}} \quad (3)$$

I(k) stands for the sum of intensities on the k-th compression image, and $I_{ref}$ is the sum of intensities on the image corresponding to the reference force $F_{ref}$. The reference image and force are chosen when a relatively large CIS image (taking up at least 25% of the screen) appears on the screen. For example, in the case of breast cancer in a human patient, this may be somewhere between 3 N and 15 N. We use sum of pixel intensity values or maximum intensity values to estimate the indentation of the probe due to the fact that the probe's deformation in the z-direction is directly proportional to the tactile image intensity change.

Softness index, Sass, is a measure of stiffness of the tissue with inclusions. It calculated as a slope of the Mobile-platform CIS stress-deformation curve computed for the tumor region:

$$S_{CISS} = \frac{\sigma_z(k)}{d_z(k)}, \quad (4)$$

Due to the Mobile-platform CIS hardware design, the elastic silicone probe deforms more rapidly while in contact with stiff inclusions than with soft ones. That causes the softness index to be inversely proportional to the true elastic modulus (Young's modulus) of the imaged inclusion. Greater $S_{CISS}$ value indicates softer tumors and lesser $S_{CISS}$ indicates harder tumors.

Absolute Elasticity Estimation Method Using Deep Learning (Deep Brief Net).

Figure 15:
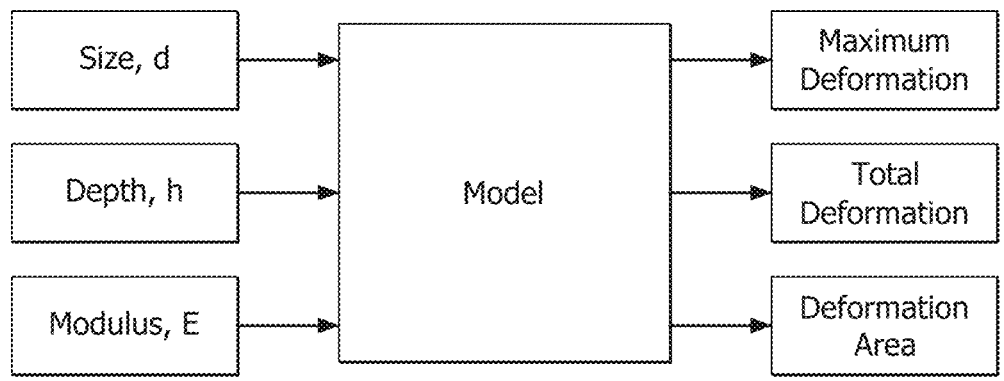
FIG. 15 is a diagram of a forward modeling method.
Figure 16:
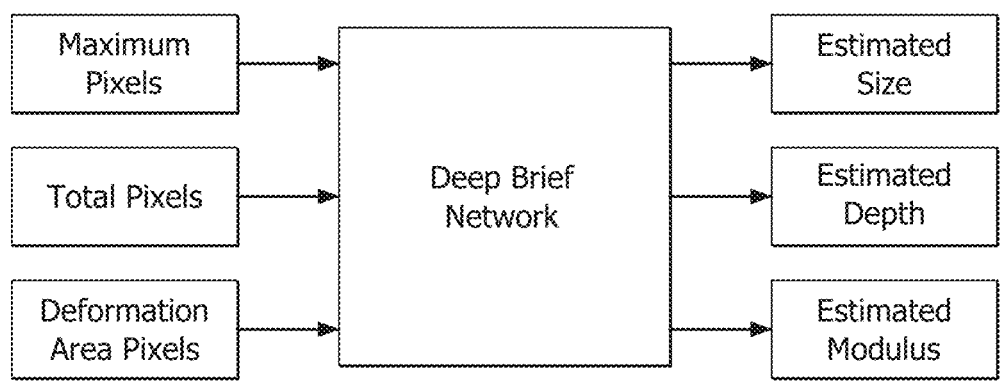
FIG. 16 is a diagram of an inverse modeling method.

Here we present a method to obtain the absolute elasticity of the target. Here the embodiment is for a human tumor application, but other applications are possible. In order to compute the absolute Young's modulus (elasticity) of the tumor, we utilize deep learning. We will model the target's mechanical properties such as size of the deformation due to elasticity. The method is divided into forward approach and inverse approach. See FIGS. 15 and 16. The forward approach provides the stress graph of the skin. The inverse approach provides elasticity of the target using deep learning as shown in FIG. 16.

Modeling and Forward Approach. The purpose of the forward algorithm is to find the relationship between tissue inclusion parameters and CIS data. Three dimensional analysis leads to a novel method of predicting the characteristics of the human tumor; it can be directly incorporated with health care provider's palpation. The Finite Element Method (FEM) is used for proving properties such as the shape, size, and elasticity of the tumors. The input parameters are:

Tissue loading (compression of the surface of the tissue), l

Indentation diameter, d

Stiffness of skin, $E_r$

The objective is to investigate the effects of the skin in a biological tissue associated with the application of loading on the tissue. We used ANSYS (Pennsylvania), an engineering simulation software package. Other modeling software can be used. The finite element model (FEM) consists of sensing probe, soft tissues (for example, representing human breast tissue), and harder inclusions (for example, representing tumors). We model the breast and tumor as elastic isotropic elements. The stress distribution is obtained from the dynamic probe image. From these models, we obtain maximum deformation, total deformation, and deformation area. The device compresses against the breast tissue with tumors. The deformation of the sensing probe is captured. We relate size, depth and elasticity of the tumor with maximum deformation, total deformation, and deformation area from the simulation.

Absolute Young's Modulus Determination using Inverse Approach. Although the results of the forward approach can show the existence of tumor, they do not provide detailed information on the tumor characteristics. One technique for solving inverse problems is using a deep learning of the forward results. The first part is the data acquisition and construction of tactile maps using the FEM. In the second part, we require an inverse model that takes a CIS map as input and produces the size and elasticity of the tissue and tumor that has been imaged as output. An inverse algorithm estimates the elastic modulus, depth, and size of the tumor from maximum deformation, total deformation, and deformation area, which are obtained from CIS. We use a deep neural network method called "Deep Brief Net" (DBN) for this inverse modeling. This DBN method improves the accuracy of the inverse algorithm (LeCun et al., 2015). A conventional Artificial Neural Network (ANN) has overfitting issues, which results in poor generalization performance. DBN can be pre-trained by an unsupervised manner to avoid the overfitting and the DBN with latent variable space in its deep structure can represent complex nonlinear functions otherwise not efficiently representable by the ANN with shallow structure (i.e., only one or two hidden layers). We use the DBN to improve the accuracy of the inverse algorithm. In this way, we propose to obtain the absolute Young's modulus of the targets.

Risk Index Determination Methods

In our embodiment, we describe a tumor risk index that we can obtain using mobile-platform CIS. We utilize quantified size and softness index information to obtain the tumor risk index. Other mechanical properties such as mobility and softness can be incorporated into this risk index. Here we describe two different embodiments of the method of determining the risk index.

Simple Weighting Method. As the first embodiment, we compute the risk index with equal weighting between size and softness. We first normalize the size between 1 and 5 with 5 being maximum size, such as 2 cm, and 1 being the minimum size, such as 2 mm. We also normalize softness to 1 to 5, with 5 being hard and 1 being soft. The range of softness may be from 0 to $250 \times 10^{-9}$/Pa, divided into the 5 levels. Then we multiply the size and softness by 0.5 and add them together. Thus, we equally weight the size information and softness information, and the risk index is a number from 1 to 5. The larger the size of the tumor, the more likely it is to be malignant. The softer the tumor, the more likely it is to be benign.

Data Classification using Convolution Neural Network Method. Another embodiment is to utilize machine learning methods such as neural network to classify the targets. The CIS signatures such as size, mobility, and elasticity of the tumor will be obtained from mobile platform CIS. Once CIS data are available, the data must be fused to develop the Tumor Characterization Model. We first create a database of size, depth, mobility, and elasticity with malignancy information. Then we use convolution neural network (CNN) to classify the tumors.

Even though the CIS data are available, characterizing tumors as malignant or benign is not simple. The computer has to fuse the information and provide the patient the probability of the lesion being malignant.

Figure 17:
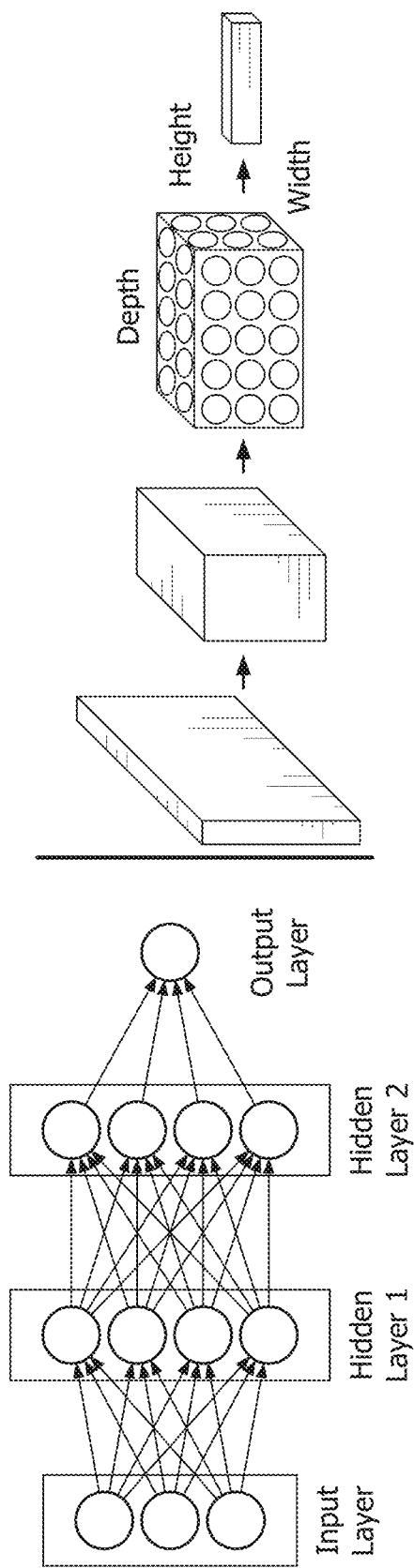
FIG. 17 is a diagram of a neural network.

Referring to FIG. 17, we use a convolution neural network (CNN) method (Ji et al. 2013) to classify the lesions using size, elasticity, and depth information. We will use the CNN for tumor classification. Convolution neural networks (CNN) are similar to neural networks, but are designed to accept images as inputs. We present the CNN architectures: convolution layer, pooling layer, and fully-connected layer. The convolution layer is denoted by the equation:

$$v_{ij}^x = g(b_{ij} + \Sigma_m \Sigma_{p=0}^{P_{i-1}} w_{ijm}^p v_{(i-1)m}^{x+p}), \quad (5)$$

where $v_{ij}^x$: is the value of a neuron at position x of the j-th feature map in the i-th layer. Each pooling layer corresponds to the previous convolution layer. We use max pooling, $$a_j = \underset{N \times 1}{\text{MAX}}(a_i^{n \times 1} u(n, 1)), \quad (6)$$

where u(n,1) is a window function to patch of the convolution layer, and $a_j$ is the maximum in the neighborhood. These layers are stacked to form a full CNN architecture. Each layer accepts 3D volume as input and transform it to an output 3D volume through a differentiable function. For breast tumor application, we obtain the CIS images and classify these images along spatial and temporal dimensions. Then we develop a CNN to classify benign and malignant tumors as the outputs.

After correlating the outputs with the tumor histopathology results, we compute the probability of tumor being malignant. This probability of a tumor being malignant will be computed as the risk index after the completion of the database.

The mobile platform Compression-induced imaging system (CIS) only utilizes the camera, communication, and limited data processing functions of the smartphone. Specific embodiments have been described using a smartphone current at the time of writing. However, as long as a camera exists and communication (Bluetooth, Wi-Fi, or some yet to be developed successor) functions exist in the smartphone, the CIS system will work. The hardware frame of the attachment and the application may need to be updated for a new smartphone, because the physical location of the camera might change. However, the principles of CIS are not dependent upon the specific functions or design of a smartphone. The app software will change depending on the type of smartphone and the versions of application creating software. For example, the embodiments described above use Xcode 8 and Swift 3.0.2. Also, the exact procedure for synchronization of the tactile image and applied force data may depend on the specific smartphone hardware and operating system. However, it will be within the ability of the ordinary skilled person to update the present teachings from time to time to remain consistent with then-current smartphone technology.

The light source aligning method, damage detection, absolute elasticity computation method, and data classification method are all relevant regardless of smartphone technology change.

It would be possible to provide a camera in the frontend attachment 24, instead of using the camera 32 of the smartphone 22. That has the advantage that it is not necessary to adjust or redesign the cradle every time the smartphone designer moves the camera, but has the disadvantage that a separate camera must be provided (at significant extra cost, because the makers of the present device do not enjoy the huge sales volume and corresponding economies of scale of the big smartphone manufacturers).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed. The various embodiments and elements can be interchanged or combined in any suitable manner as necessary. Thus any features described in the specification and dependent claims should be understood as being useful in and combinable with other embodiments and other claims.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

REFERENCES CITED

The following prior publications, some of which are discussed above, are incorporated herein by reference as if explicitly set forth herein.

Dargahi, J., and Najarian, S., "Human tactile perception as a standard for artificial tactile sensing—a review," *International journal of medical robotics and computer assisted surgery*, Vol. 1, No. 1, pp. 23-35, 2004.

Itoh A, Ueno E, Tohno E, Kamma H, Takahashi H, Shiina T, et al. Breast disease: Clinical application of US elastography for diagnosis. Radiology. 2006; 239:341-50. [PubMed: 16484352]

Ji S., Yang M., and Yu K., "3D Convolutional Neural Networks for Human Action Recognition," PAMI, vol. 35, no. 1, pp. 221-31, 2013.

Krouskop, T., Wheeler T., Kallel F., Garra B., (1998) "Elastic Moduli of Breast and Prostate Tissues Under Compression," *Ultrasonic Imaging*, Vol. 20, pp. 260-274.

LeCun Y., Bengio Y., and Hinton G., "Deep Learning," Nature, vol. 521, no. 7553, pp. 436-444, 2015.

Regini, E., Bagnera S., Tota D., Capanino P., Luparia A., Barisone F., Durando M., Mariscotti G., Gandini G., (2010) "Role of sonoelastography in characterizing breast nodules. Preliminary experience with 120 lesions," Radiol. Med. (La Radiologia. *Medica*.) Springer. Feb. 22, 2010.

Rivaz, H., Boctor, E, Foroughi, P, Zellars, R, Fichtinger, G, Hager G, (2008) "Ultrasound elastography: a dynamic programming approach," IEEE Trans Med Imaging, Vol. 27, No. 10, pp. 1373-1377.

The invention claimed is:

1. A mobile-platform imaging device that uses compression of a target region to generate an image of an object, comprising:

a tactile sensor comprising an optical waveguide with a front surface arranged for contacting the target region, the optical waveguide comprising at least a first layer at the front surface that is flexible and transparent, the tactile sensor further comprising at least one light source configured to direct light into the optical waveguide, wherein the optical waveguide is configured so that at least some of the light directed into the optical waveguide is scattered out of the first layer when the first layer is deformed, and wherein the first layer is deformed by the tactile sensor being pressed against the target region;

at least one force sensor that detects a force being applied to press the tactile sensor against the target region and outputs corresponding force information, the force sensor mounted so as to permit calculation of an applied force in a direction normal to the front surface of the optical waveguide;

a first communication unit connected to receive the force information from the force sensor and to associate with the force information a force time when the force information was obtained; and a receptacle for holding a mobile device having a second communication unit and an imager so positioned that the imager can generate image information using at least some of the light scattered out of the first layer;

wherein the first communication unit is configured to communicate with the second communication unit and the mobile device is configured to communicate with an external network; and wherein the second communication unit is programmed to control activation of the imager and, when the imager is activated to capture an image, to associate an image time with the captured image, and to retrieve from the first communication unit the force information that was received from the force sensor at the force time that the image was captured, the second communication unit further programmed to associate the captured image with the calculated normal applied force at the common force time and image time;

the mobile-platform imaging device configured to perform the following steps:

determine a contact area of the applied force associated with the image information that is generated for each image by the imager from light scattered out of the first layer due to each applied force;

determine stress for each image from the contact area of the tactile sensor and the force information;

determine a softness index of the object based on a deformation in each image associated with the applied force and the determined stress for each image in accordance with the following equation:

$$S_{CISS} = \frac{\sigma_z(k)}{d_z(k)},$$

where $\sigma_z(k)$ is the stress calculated in the normal direction for each image (k), and $d_z(k)$ is a deformation ratio for each image (k); and determine a risk index for the softness index of the object and an estimated size of the object at least the softness index of the object.

2. The mobile-platform imaging device of claim 1, wherein the tactile sensor comprises multiple light sources configured to direct light into the optical waveguide, the optical waveguide configured to constrain the light within the optical waveguide when the optical waveguide is not deformed.

3. The mobile-platform imaging device of claim 2, wherein the tactile sensor comprises a diffuser positioned adjacent to the light sources for diffusing light from the light sources to cause the light to distribute uniformly within the optical waveguide.

4. The mobile-platform imaging device of claim 2, further comprising a constant current driver circuitry for powering the light sources.

5. The mobile-platform imaging device of claim 1, further comprising a support structure for maintaining the optical waveguide in place when force is applied to the optical waveguide, the support structure comprising a rigid frame mounted against a rear surface of the optical waveguide spaced apart from the front surface for inhibiting deformation of the rear surface, the rigid frame defining a holder having a cutout for installation therein of the optical waveguide, the rigid support configured so as to not obstruct the capture of scattered light from the optical waveguide.

6. The mobile-platform imaging device of claim 5, wherein an aperture is formed centered within the cutout for providing the line of sight between an imaging unit of the mobile device and the optical waveguide.

7. The mobile-platform imaging device of claim 5, wherein the tactile sensor comprises multiple light sources and multiple holes are formed spaced about the holder for installation of the light sources for providing selective side-illumination of the optical waveguide.

8. The mobile-platform imaging device of claim 1, wherein the at least one force sensor comprises a plurality of force sensors, each force sensor configured to provide a signal for determining a force being applied by the tactile sensor against the target region, the signals from the sensors providing information for calculating the normal applied force.

9. The mobile-platform imaging device of claim 1, wherein the force sensor is located between the tactile sensor and the receptacle for holding the mobile device.

10. The mobile-platform imaging device of claim 1, further comprising a handle, wherein the force sensor is located between the handle and the receptacle for holding the mobile device.

11. The mobile-platform imaging device of claim 10, wherein the handle is defined by a frame of the receptacle.

12. The mobile-platform imaging device of claim 10, wherein the handle is defined by a housing operably installed on the frame.

13. The mobile-platform imaging device of claim 12, further comprising a motor operably installed on the housing for controlled application of the force to the tactile sensor through the receptacle as sensed by the force sensor.

14. The mobile-platform imaging device of claim 1, further comprising a motor operably installed on the receptacle for controlled application of the force to the tactile sensor through the receptacle as sensed by the force sensor.

15. The mobile-platform imaging device of claim 1, wherein the mobile device is a mobile telephone programmed to generate the image information, synchronize the image information with the force information, and transmit associated information to an external device.

16. The mobile-platform imaging device of claim 15, wherein the associated information further includes information selected from a current date, a current time, a user D of a current user of the mobile device, and a target ID of the object.

17. The mobile-platform imaging device of claim 1, wherein at least the first layer of the optical waveguide is one of curved, semi-spherical, rectangular.

18. The mobile-platform imaging device of claim 1, wherein at least the first layer of the optical waveguide is Polydimethylsiloxane (PDMS) elastomer.

19. A method of determining a risk index for an object based on a surface or subsurface size of the object and a softness index of the object using a mobile-platform imaging device that uses compression of a target region to generate an image of the object, the mobile imaging device comprising:

a tactile sensor comprising an optical waveguide comprising at least a first layer that is flexible and transparent, the tactile sensor further comprising at least one light source configured to direct light into the optical waveguide, wherein the optical waveguide is configured so that at least some of the light directed into the optical waveguide is scattered out of the first layer when the first layer is deformed, and wherein the first layer is deformed by the tactile sensor being pressed against the target region;

a force sensor that detects a force being applied to press the tactile sensor against the target region and outputs corresponding force information, the force sensor mounted so as to permit calculation of an applied force in a direction normal to the front surface of the optical waveguide;

a first communication unit connected to receive the force information from the force sensor; and a receptacle for holding a mobile device having a second communication unit and an imager so positioned that the imager can generate image information using at least some of the light scattered out of the first layer;

wherein the first communication unit is configured to communicate with the second communication unit and the mobile device is configured to communicate with an external network;

the method comprising the steps of:

obtaining the image information and corresponding force information at the second communication unit;

calculating the applied force in a direction normal to the front surface of the optical waveguide from the respective force information associated with the corresponding image information;

determining a number of pixels in the image of the object corresponding to the image information associated with the calculated normal applied force;

estimating the size of the object using 3D interpolation based on the number of pixels in the image of the object and the calculated normal applied force associated with the image of the object;

determining a contact area of the applied force associated with the image information that is generated for each image by the imager from light scattered out of the first layer due to each applied force;

determining stress for each image (k) from the contact area of the tactile sensor and the force information in accordance with the following equation:

$$\sigma_z(k) = \frac{F(k) - F_{ref}}{A_C}$$

where F(k) is the applied force in the z direction, $F_{ref}$ is the force value taken at a reference point, and $A_c$ is the contact area;

determining a deformation ratio for each image (k) in accordance with the following equation:

$$d_z(k) = \frac{|I(k) - I_{ref}|}{I_{ref}}$$

where I(k) is the sum of intensities on the k-th compression image, and $I_{ref}$ is the sum of intensities on the image corresponding to the reference force $F_{ref}$;

determining a softness index of the object based on the deformation ratio for for each image (k) associated with the applied force F(k) and the determined stress $\sigma_z(k)$ for each image (k) in accordance with the following equation:

$$S_{CISS} = \frac{\sigma_z(k)}{d_z(k)},$$

where $v_z(k)$ is the stress calculated in the normal direction for each image (k), and $d_z(k)$ is the deformation ratio for each image (k); and determining a risk index for the object based on the estimated size of the object and the softness index of the object.

20. A method of determining a risk index for an object based on a surface or subsurface size of the object and a softness index of the object using a mobile-platform imaging device that uses compression of a target region to generate an image of the object, the mobile imaging device comprising:

a tactile sensor comprising an optical waveguide comprising at least a first layer that is flexible and transparent, the tactile sensor further comprising at least one light source configured to direct light into the optical waveguide, wherein the optical waveguide is configured so that at least some of the light directed into the optical waveguide is scattered out of the first layer when the first layer is deformed, and wherein the first layer is deformed by the tactile sensor being pressed against the target region;

a force sensor that detects a force being applied to press the tactile sensor against the target region and outputs corresponding force information;

a first communication unit connected to receive the force information from the force sensor and to associate with the force information a force time when the force information was obtained; and a receptacle for holding a mobile device having a second communication unit and an imager so positioned that the imager can generate image information using at least some of the light scattered out of the first layer;

wherein the first communication unit is configured to communicate with the second communication unit and the mobile device is configured to communicate with an external network; and wherein the second communication unit is programmed to control activation of the imager and, when the imager is activated to capture an image, to associate an image time with the captured image, and to retrieve from the first communication unit the force information that was received from the force sensor at the force time that the image was captured, the second communication unit further programmed to associate the captured image with the force information at the common force time and image time;

the method comprising the steps of:

activating the imager to capture the image;

associating an image time with the captured image;

retrieving from the first communication unit the force information that was received from the force sensor at the image time;

associating with the force information a force time when the force information was obtained for the captured image, the force time being common with the image time;

associating the captured image with the retrieved force information at the common force time and image time;

estimating the size of the object using 3D interpolation based on the captured image and the associated force information;

determining a contact area of the applied force associated with the image information that is generated for each image by the imager from light scattered out of the first layer due to each applied force, determining stress for each image from the contact area of the tactile sensor and the force information;

determining a softness index of the object based on a deformation in each image associated with the applied force and the determined stress for each image in accordance with the following equation:

$$S_{CISS} = \frac{\sigma_z(k)}{d_z(k)},$$

where $\sigma_z(k)$ is the stress calculated in the normal direction for each image (k), and $d_z(k)$ is a deformation ratio for each image (k); and determining a risk index for the object based on the estimated size of the object and the softness index of the object.

* * * * *

UNITED STATES PATENT AND TRADEMARK OFFICE
CERTIFICATE OF CORRECTION

PATENT NO. : 11,940,650 B2
APPLICATION NO. : 17/957178
DATED : March 26, 2024
INVENTOR(S) : Chang-Hee Won It is certified that error appears in the above-identified patent and that said Letters Patent is hereby corrected as shown below:

In the Claims

In Claim 1, Column 23, Lines 9-11, please delete the text and replace it with:
--determine a risk index for the object based on the softness index of the object and an estimated size of the object.--

Signed and Sealed this
Thirtieth Day of July, 2024

Katherine Kelly Vidal
*Director of the United States Patent and Trademark Office*